United States Patent [19]

Hornback et al.

[11] Patent Number: 5,578,608
[45] Date of Patent: Nov. 26, 1996

[54] SYMMETRICAL DIARYL AND DIHETEROANYL CIS EPOXY ALKANES ANTIVIRAL COMPOUNDS

[75] Inventors: William J. Hornback; John E. Munroe, both of Indianapolis, Ind.

[73] Assignee: Eli Lilly and Company, Indianapolis, India.

[21] Appl. No.: 372,722

[22] Filed: Jan. 17, 1995

Related U.S. Application Data

[63] Continuation of Ser. No. 177,650, Jan. 5, 1994, abandoned, which is a continuation of Ser. No. 901,447, Jun. 19, 1992, abandoned.

[51] Int. Cl.⁶ .................. A61K 31/47; A61K 31/415; A61K 31/335; C07D 215/38; C07D 303/36; C07D 303/08
[52] U.S. Cl. .................. 514/314; 514/311; 514/397; 514/400; 514/475; 546/175; 546/281.7; 546/256; 548/311.1; 548/365.7; 549/553
[58] Field of Search .................. 546/175, 268; 549/553; 514/311, 314, 475

[56] References Cited

U.S. PATENT DOCUMENTS

| | | | |
|---|---|---|---|
| 4,788,204 | 11/1988 | Benavides et al. | 546/175 X |
| 5,142,056 | 8/1992 | Kempe et al. | 549/553 X |
| 5,155,227 | 10/1992 | Boder | 546/175 X |

FOREIGN PATENT DOCUMENTS

| | | | |
|---|---|---|---|
| 0402646 | 5/1990 | European Pat. Off. | 546/314 |
| 60-193979 | 2/1985 | Japan | 549/553 |

OTHER PUBLICATIONS

"Synthetic Non–peptide Inhibitors of HIV Protease", Blumenstein, J. J., et al., Biochem. and Biophys. Res. Comm. 163(2), pp. 980–987 (1989).

"The Carboxylate Ion in the Active Center of Pepsin", Hartsuck, J. A., et al., The J. of Biol. Chem., 247(8), pp. 2575–2580 (1972).

"In Vitro Inhibition of HIV–1 Proteinase by Cerulenin", Moelling, K., et al., FEBS Letters (1990), pp. 373–377.

"Peptidyl Expoxides as Potent, Active Site–directed Irreversible Inhibitors of HIV–1 Protease", Moore, M. L. et al., *Peptides Chemistry and Biology*, Proceedings of the Twelfth American Peptide Symposium, Jun. 16–21, 1991, edited by John A. Smith and Jean E. Rivier, pp. 781–782 (1992).

"Design, Synthesis and Characterization of an Irreversible Inhibitor of HIV–1 Protease", Kaldor, S. W. et al., Abstr. No. 178, 203rd ACS National Meeting (Apr. 5–10, 1992).

"Human Immunodeficiency Virus 1 Protease Expressed in *Escherichia coli* behaves as a Dimeric Aspartic Protease", Meek, T. D. et al., Proc. Natl. Acad. Sci. USA, 86, pp. 1841–1845 (1989).

*Primary Examiner*—Floyd D. Higel
*Attorney, Agent, or Firm*—Janet T. McClain

[57] ABSTRACT

An HIV protease inhibiting compound of formula I

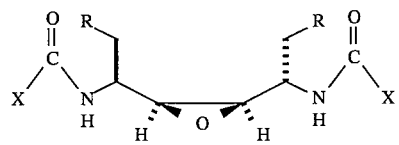

wherein:

R is $C_1$–$C_6$ alkyl, cycloalkyl, heterocycle, unsaturated heterocycle, aryl, cycloalkyl ($C_1$–$C_4$)alkyl, heterocycle($C_1$–$C_4$)alkyl, unsaturated heterocycle ($C_1$–$C_4$)alkyl, aryl($C_1$–$C_4$)alkyl, or —A—$(CH_2)_q$—$R^0$, where A is —O—, —NH— or —S—; q is 0, 1, 2 or 3; and $R^0$ is cycloalkyl, aryl, heterocycle or unsaturated heterocycle;

X is 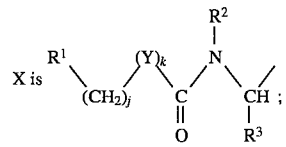

where $R^1$ is aryl, cycloalkyl, heterocycle or unsaturated heterocycle; $R^2$ is hydrogen or $C_1$–$C_4$ alkyl; $R^3$ is an amino acid side chain, —$CH_2CH_3$, —$CH_2CH_2CH_3$, —$CH_2(CH_2)_2CH_3$, —$C(CH_3)_3$, cyano($C_1$–$C_4$)alkyl, unsaturated heterocycle ($C_1$–$C_4$)alkyl, aryl($C_1$–$C_4$)alkyl, —$(CH_2)_s$—$A^0$—$(CH_2)_r$—$R^4$, or —$CH_2$—C(O)—$NR^2$—$(CH_2)_r$—$R^5$, where s is 1, 2, 3 or 4; r is 0, 1, 2 or 3; $A^0$ is —O—, —NH— or —S—; $R^4$ is $C_1$–$C_6$ alkyl, cycloalkyl, aryl, heterocycle or unsaturated heterocycle; $R^5$ is cycloalkyl, aryl, heterocycle or unsaturated heterocycle; j is 0, 1, 2, 3 or 4; k is 0 or 1; and Y is —O—, —N($R^2$)— or —S—; or a pharmaceutically acceptable salt thereof.

24 Claims, No Drawings

SYMMETRICAL DIARYL AND DIHETEROANYL CIS EPOXY ALKANES ANTIVIRAL COMPOUNDS

This application is a continuation of application Ser. No. 08/177,650, filed Jan. 5, 1994, now abandoned, which is a continuation of application Ser. No. 07/901,447, filed Jun. 19, 1992, now abandoned.

BACKGROUND OF THE INVENTION

A retrovirus designated human immuno-deficiency virus (HIV) is the causative agent of the complex disease termed Acquired Immune Deficiency Syndrome (AIDS), and is a member of the lentivirus family of retroviruses. M. A. Gonda, F. Wong-Staal, R. C. Gallo, "Sequence Homology and Morphological Similarity of HTLV III And Visna Virus, A Pathogenic Lentivirus", Science, 227, 173, (1985); P. Sonigo, N. Alizon, et al., "Nucleotide Sequence of the Visna Lentivirus: Relationship to the AIDS Virus", Cell, 42, 369, (1985). The complex disease AIDS includes progressive destruction of the immune system and degeneration of the central and peripheral nervous systems. The HIV virus was previously known or referred to as LAV, HTLV-III or ARV.

A common feature of retrovirus replication is the post-translational processing of precursor polyproteins by a virally encoded protease to generate mature viral proteins required for viral assembly and function. Interruption of this processing appears to prevent the production of normally infectious virus. Unprocessed structural proteins also have been observed in clones of non-infectious HIV strains isolated from human patients. The results suggest that the inhibition of HIV protease represents a viable method for the prevention or treatment of AIDS and the prevention or treatment of infection by HIV.

The HIV genome encodes structural protein precursors known as gag and pol, which are processed to afford the protease, reverse transcriptase and endonuclease/integrase. The protease further cleaves gag and gag-pol polyproteins to yield mature structural proteins of the virus core.

Considerable efforts are being directed toward the control of HIV by means of the structural protein precursors which are processed to yield the retroviral protease, reverse transcriptase and endonuclease/integrase. For example, a currently used therapeutic, AZT, is an inhibitor of the viral reverse transcriptase. H. Mitsuya, NS. Broder, "Inhibition of the In Vitro Infectivity in Cytopathic Effects of HTLV III", Proc. Natl. Acad. Sci. USA, 83, 1911 (1986).

Research efforts have also been directed toward HIV protease inhibitors. For example, European Patent Application (EPA) 361 341; EPA 346 847; EPA 402 646; and EPA 337 714 disclose compounds which are said to be useful as HIV protease inhibitors.

Unfortunately, many of the known HIV protease inhibitors suffer from toxicity problems, lack of bioavailability or short in vivo half-lives.

Despite the recognized therapeutic potential associated with a protease inhibitor and the research efforts expended thus far, a viable therapeutic agent has not yet emerged.

Accordingly, a primary object of the present invention is to provide novel HIV protease inhibitors which are useful in the treatment of AIDS.

A further object of the present invention is to provide therapeutic compositions that are of value in the prevention and/or treatment of infection by HIV and the treatment of the resulting acquired immune deficiency syndrome.

Still another object is to provide methods for the prevention and/or treatment of infection by HIV and the resulting acquired immune deficiency syndrome.

other objects, features and advantages will become apparent to those skilled in the art from the following description and claims.

SUMMARY OF THE INVENTION

The present invention relates to compounds of formula I and the pharmaceutically acceptable salts thereof, that inhibit the protease encoded by human immunodeficiency virus (HIV) type 1 (HIV-1) and type 2 (HIV-2). These compounds are useful in the treatment or prevention of infection by HIV and the treatment or prevention of the resulting acquired immune deficiency syndrome (AIDS). The compounds, pharmaceutically acceptable salts and pharmaceutical compositions, of the invention can be used alone or in combination with other antivirals, immunomodulators, antibiotics or vaccines. Methods of treating or preventing AIDS, methods of treating or preventing infection by HIV and methods for inhibiting HIV replication are disclosed.

The present invention relates to a method for inhibiting HIV replication in an HIV infected cell, in a cell susceptible to HIV infection or in a primate in need thereof, thus treating or preventing both HIV infection and AIDS, comprising administering a compound of formula I

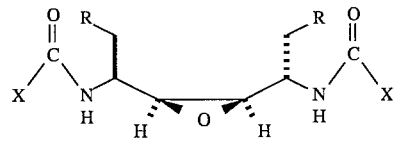

wherein:

R is $C_1$–$C_6$ alkyl, cycloalkyl, heterocycle, unsaturated heterocycle, aryl, cycloalkyl($C_1$–$C_4$)alkyl, heterocycle($C_1$–$C_4$)alkyl, unsaturated heterocycle ($C_1$–$C_4$)alkyl, aryl($C_1$–$C_4$)alkyl, or a structure having the formula —A—$(CH_2)_q$—$R^0$, where A is —O—, —NH— or —S—;

q is 0, 1, 2 or 3;

$R^0$ is cycloalkyl, aryl, heterocycle or unsaturated heterocycle;

X is

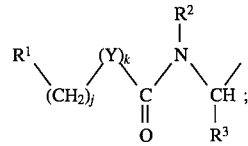

where:

$R^1$ is aryl, cycloalkyl, heterocycle or unsaturated heterocycle;

$R^2$ is hydrogen or $C_1$–$C_4$ alkyl;

$R^3$ is an amino acid side chain, —$CH_2CH_3$, —$CH_2CH_2CH_3$, —$CH_2(CH_2)_2CH_3$, —$C(CH_3)_3$, cyano($C_1$–$C_4$)alkyl, unsaturated heterocycle($C_1$–$C_4$)alkyl, aryl($C_1$–$C_4$)alkyl or a structure having the formula —$(CH_2)_s$—$A^0$—$(CH_2)_r$—$R^4$ or —$CH_2$—C(O)—$NR^2$—$(CH_2)_r$—$R^5$, where s is 1, 2, 3 or 4;

r is 0, 1, 2 or 3;

$A^0$ is —O—, —NH— or —S—;

$R^4$ is $C_1$–$C_6$ alkyl, cycloalkyl, aryl, heterocycle or unsaturated heterocycle;

$R^5$ is cycloalkyl, aryl, heterocycle or unsaturated heterocycle;

j is 0, 1, 2, 3 or 4;

k is 0 or 1; and

Y is —O—, —N($R^2$)— or —S—;

or a pharmaceutically acceptable salt thereof.

The present invention also relates to a compound of formula I, or a pharmaceutically acceptable salt thereof, wherein x and R are as defined above.

The present invention further provides pharmaceutical formulations comprising a compound of formula I, or a pharmaceutically acceptable salt thereof, in combination with a pharmaceutically acceptable carrier, diluent or excipient therefor.

In addition, the present invention provides useful intermediates of formulae Ia

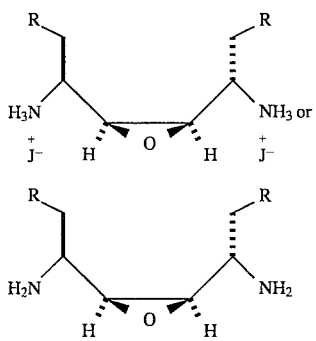

wherein:

R is $C_1$–$C_6$ alkyl, cycloalkyl, heterocycle, unsaturated heterocycle, aryl, cycloalkyl ($C_1$–$C_4$)alkyl, heterocycle($C_1$–$C_4$)alkyl, unsaturated heterocycle ($C_1$–$C_4$)alkyl, aryl($C_1$–$C_4$)alkyl, or a structure having the formula —A—$(CH_2)_q$—$R^0$, where A is —O—, —NH— or —S—;

q is 0, 1, 2 or 3;

$R^0$ is cycloalkyl, aryl, heterocycle or unsaturated heterocycle; and

J is halide, methanesulfonate, benzenesulfonate, p-toluenesulfonate, acetate or trifluoroacetate.

DETAILED DESCRIPTION OF THE INVENTION

The present invention provides new compounds of formula I, as described supra, that are useful for treating or preventing both HIV infection and AIDS.

All temperatures stated herein are in degrees Celsius (°C.). All units of measurement employed herein are in weight units except for liquids which are in volume units.

As used herein, the term "$C_1$–$C_6$ alkyl" represents a straight or branched alkyl chain having from one to six carbon atoms. Typical $C_1$–$C_6$ alkyl groups include methyl, ethyl, propyl, isopropyl, butyl, isobutyl, sec-butyl, t-butyl, pentyl, neo-pentyl, hexyl and the like. The term "$C_1$–$C_6$ alkyl" includes within its definition the term "$C_1$–$C_4$ alkyl".

"Halo" represents chloro, fluoro, bromo or iodo.

"Halo($C_1$–$C_4$)alkyl" represents a straight or branched alkyl chain having from one to four carbon atoms with 1–3 halogen atoms attached to it. Typical halo($C_1$–$C_4$)alkyl groups include chloromethyl, 2-bromoethyl, 1-chloroisopropyl, 2,3-difluoropropyl, 3-bromobutyl, 3-chloroisobutyl, iodo-t-butyl, trifluoromethyl and the like.

"Cyano($C_1$–$C_4$)alkyl" represents a straight or branched alkyl chain having from one to four carbon atoms with a cyano group attached to it. Typical cyano($C_1$–$C_4$)alkyl groups include cyanomethyl, 2-cyanoethyl, 3-cyanopropyl, 2-cyanoisopropyl, 4-cyanobutyl and the like.

"$C_1$–$C_4$ alkylthio" represents a straight or branched alkyl chain having from one to four carbon atoms attached to a sulfur atom. Typical $C_1$–$C_4$ alkylthio groups include methylthio, ethylthio, propylthio, isopropylthio, butylthio and the like.

"$C_1$–$C_4$ alkylthio($C_1$–$C_4$)alkyl" represents a straight or branched alkyl chain containing from one to four carbon atoms with a $C_1$–$C_4$ alkylthio group attached to it. Typical $C_1$–$C_4$ alkylthio($C_1$–$C_4$)alkyl groups include methylthioethyl, ethylthiobutyl, propylthioisopropyl, isopropylthiomethyl, butylthioethyl and the like.

"$C_1$–$C_4$ alkylamino" represents a straight or branched alkylamino chain having from one to four carbon atoms attached to a nitrogen atom. Typical $C_1$–$C_4$ alkylamino groups include methylamino, ethylamino, propylamino, isopropylamino, butylamino, sec-butylamino and the like.

"Di($C_1$–$C_4$)alkylamino" represents a straight or branched dialkylamino chain having two alkyl chains of from one to four carbon atoms attached to a common nitrogen atom. Typical di($C_1$–$C_4$)alkylamino groups include dimethylamino, ethylmethylamino, methylisopropylamino, t-butylisopropylamino, di-t-butylamino and the like.

"$C_1$–$C_4$ alkoxy" represents a straight or branched alkyl chain having from one to four carbon atoms attached to an oxygen atom. Typical $C_1$–$C_4$ alkoxy groups include methoxy, ethoxy, propoxy, isopropoxy, butoxy and the like.

"$C_1$–$C_4$ alkoxycarbonyl" represents a straight or branched alkoxy chain having from one to four carbon atoms attached to a carbonyl moiety. Typical $C_1$–$C_4$ alkoxycarbonyl groups include methoxycarbonyl, ethoxycarbonyl, propoxycarbonyl, isopropoxycarbonyl, butoxycarbonyl, t-butoxycarbonyl and the like.

"Carbamoyl($C_1$–$C_4$)alkyl" represents a straight or branched alkyl chain having from one to four carbon atoms with a carbamoyl group attached to it. Typical carbamoyl ($C_1$–$C_4$)alkyl groups include carbamoylmethyl, carbamoylethyl, carbamoylpropyl, carbamoylisopropyl, carbamoylbutyl and carbamoyl-t-butyl and the like.

"Cycloalkyl" represents a saturated hydrocarbon ring structure containing from three to eight carbon atoms which is unsubstituted or substituted with 1, 2 or 3 substituents independently selected from halo, halo ($C_1$–$C_4$) alkyl, $C_1$–$C_4$ alkyl, $C_1$–$C_4$ alkoxy, carboxy, $C_1$–$C_4$ alkoxycarbonyl, carbamoyl, $C_1$–$C_4$ alkylcarbamoyl, amino, $C_1$–$C_4$ alkylamino, di($C_1$–$C_4$)alkylamino or a group having the structure —$(CH_2)_a$—$R^7$ where a is 1, 2, 3 or 4 and $R^7$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino. Typical cycloalkyl groups include cyclopropyl, cyclobutyl, cyclopentyl, cyclohexyl, cycloheptyl and cyclooctyl. The cycloalkyl "Cycloalkyl($C_1$–$C_4$)alkyl" represents a straight or branched alkyl chain having from one to four carbon atoms with a cycloalkyl group attached to it. Typical cycloalkyl ($C_1$–$C_4$)alkyl groups include cyclopropylmethyl, 2-cyclobutylethyl, 3-cyclopentylpropyl, 2-cyclohexylisopropyl, 4-cycloheptylbutyl and the like.

The term "heterocycle" represents an unsubstituted or substituted stable 5- to 7-membered monocyclic and stable 7- to 10-membered bicyclic heterocyclic ring which is saturated and which consists of carbon atoms and from one to three heteroatoms selected from the group consisting of nitrogen, oxygen or sulfur, and wherein any nitrogen and sulfur heteroatoms may optionally be oxidized, and any nitrogen heteroatom may optionally be quaternized and including a bicyclic group in which any of the above-defined heterocyclic rings is fused to a benzene ring. The heterocyclic ring may be attached at any heteroatom or carbon atom which affords a stable structure. The heterocycle is unsubstituted or substituted with 1, 2 or 3 substituents independently selected from halo, halo($C_1$–$C_4$)alkyl, $C_1$–$C_4$ alkyl, $C_1$–$C_4$ alkoxy, carboxy, $C_1$–$C_4$ alkoxycarbonyl, carbamoyl, $C_1$–$C_4$ alkylcarbamoyl, amino, $C_1$–$C_4$ alkylamino, di($C_1$–$C_4$)alkylamino or a group having the structure —$(CH_2)_a$—$R^7$ where a is 1, 2, 3 or 4; and $R^7$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino.

The term "unsaturated heterocycle" represents an unsubstituted or substituted stable 5- to 7-membered monocyclic and stable 7- to 10-membered bicyclic heterocyclic ring which has one or more double bonds and which consists of carbon atoms and from one to three heteroatoms selected from the group consisting of nitrogen, oxygen or sulfur, and wherein the nitrogen and sulfur heteroatoms may optionally be oxidized, and the nitrogen heteroatom may optionally be quarternized and including a bicyclic group in which any of the above-defined heterocyclic rings is fused to a benzene ring. The unsaturated heterocyclic ring may be attached at any heteroatom or carbon atom which affords a stable structure. The unsaturated heterocycle is unsubstituted or substituted with 1, 2 or 3 substituents independently selected from halo, halo($C_1$–$C_4$)alkyl, $C_1$–$C_4$ alkyl, $C_1$–$C_4$ alkoxy, carboxy, $C_1$–$C_4$ alkoxycarbonyl, carbamoyl, $C_1$–$C_4$ alkylcarbamoyl, amino, $C_1$–$C_4$ alkylamino, di($C_1$–$C_4$)alkylamino or a group having the structure —$(CH_2)_a$—$R^7$ where a is 1, 2, 3 or 4; and $R^7$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino.

Examples of such heterocycles and unsaturated heterocycles include piperidinyl, piperazinyl, 2-oxopiperazinyl, 2-oxopiperidinyl, 2-oxopyrrolodinyl, 2-oxoazepinyl, azepinyl, pyrrolyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazolyl, benzopyranyl, benzothiazolyl, benzoazolyl, furyl, tetrahydrofuryl, tetrahydropyranyl, thienyl, benzothienyl, thiamorpholinyl, thiamorpholinylsulfoxide, thiamorpholinylsulfone, oxadiazolyl, triazolyl, tetrahydroquinolinyl and tetrahydrisoquinolinyl.

"Heterocycle($C_1$–$C_4$)alkyl" represents a straight or branched alkyl chain having from one to four carbon atoms with a heterocycle group attached to it. "Unsaturated heterocycle($C_1$–$C_4$)alkyl" represents a straight or branched alkyl chain having from one to four carbon atoms with an unsaturated heterocycle group attached to it. Typical heterocycle($C_1$–$C_4$)alkyl and unsaturated heterocycle ($C_1$–$C_4$)alkyl groups include pyrrolylmethyl, quinolinylmethyl, 1-indolylethyl, 2-furylethyl, 3-thien-2-ylpropyl, 1-imidazolylisopropyl, 4-thiazolylbutyl and the like.

"Aryl" represents a phenyl or naphthyl ring. The phenyl or naphthyl ring is optionally substituted with 1, 2 or 3 substituents independently selected from halo, $C_1$–$C_4$ alkyl, $C_1$–$C_4$ alkoxy, carboxy, $C_1$–$C_4$ alkoxycarbonyl, carbamoyl, carbamoyl($C_1$–$C_4$)alkyl, amino, $C_1$–$C_4$ alkylamino, di($C_1$–$C_4$)alkylamino or a group of the formula —$(CH_2)_a$—$R^7$ where a is 1, 2, 3 or 4; and $R^7$ is hydroxy, $C_1$–$C_4$ alkoxy, carboxy, $C_1$–$C_4$ alkoxycarbonyl, amino, carbamoyl, $C_1$–$C_4$ alkylamino or di ($C_1$–$C_4$)alkylamino.

"Aryl($C_1$–$C_4$)alkyl" represents a straight or branched alkyl chain having from one to four carbon atoms with an aryl group attached to it. Typical aryl($C_1$–$C_4$)alkyl groups include phenylmethyl, 2-phenylethyl, 3-naphthylpropyl, 1-naphthylisopropyl, 4-phenylbutyl and the like.

The term "amino acid side chains" represents the distinctive atom or group bonded to the α-carbon atom of an amino acid, also having bonded thereto a carboxyl group and an amino group. These side chains are selected from those found on the following amino acids:

| | |
|---|---|
| Alanine | Ala |
| Arginine | Arg |
| Asparagine | Asn |
| Aspartic acid | Asp |
| Cysteine | Cys |
| Glutamine | Gln |
| Glutamic acid | Glu |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

The term "amino-protecting group" as used in the specification refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxy-carbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)ethoxycarbonyl, 2-(methylsulfonyl)ethoxycarbonyl, 2-(triphenylphosphino)ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-nitrophenylsulfenyl group, the diphenylphosphine oxide group and like amino-protecting groups. The species of amino-protecting group employed is not critical so long as the derivatized amino group is stable to the condition of subsequent reaction(s) on other positions of the intermediate molecule and can be selectively removed at the appropriate point without disrupting the remainder of the molecule including any other amino-protecting group(s). Preferred amino-protecting groups are t-butoxycarbonyl and benzyloxycarbonyl. Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and sons, New York, N.Y., 1981, Chapter 7.

The term "carboxy-protecting group" as used in the specification refers to substituents of the carboxy group commonly employed to block or protect the carboxy functionality while reacting other functional groups on the compound. Examples of such carboxy-protecting groups include methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylene-dioxybenzyl, benzhydryl, 4,4'-dimethoxybenzhydryl, 2,2',4,4'-tetramethoxybenzhydryl, t-butyl, t-amyl, trityl, 4-methoxytrityl, 4,4'-dimethoxytrityl, 4,4',4"- trimethoxytrityl, 2-phenylprop-2-yl, trimethylsilyl, t-butyldimethylsilyl, phenacyl, 2,2,2-trichloroethyl, β-(di(butyl)methylsilyl)ethyl, p-toluenesulfonylethyl, 4-nitrobenzylsulfonylethyl, allyl, cinnamyl, 1-(trimethylsilylmethyl)prop-1-en-3-yl and like moieties. The preferred carboxy-protecting group is benzhydryl. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

The compounds of the present invention have at least four asymmetric centers as denoted by the asterisks in the formulae below.

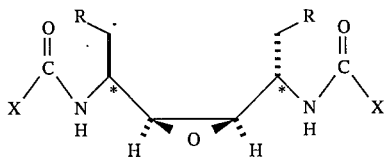

where X is

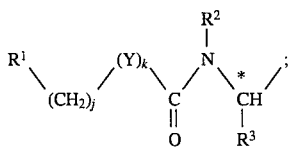

As a consequence of these chiral centers, the compounds of the present invention occur as racemates, racemic mixtures and as individual enantiomers. All asymmetric forms, individual isomers and combinations thereof, are within the scope of the present invention.

As mentioned above, the invention includes the pharmaceutically acceptable salts of the compounds defined by formula I. Although generally neutral, a compound of this invention can possess a sufficiently acidic, a sufficiently basic, or both functional groups, and accordingly react with any of a number of inorganic bases, and inorganic and organic acids, to form a pharmaceutically acceptable salt. The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a pharmaceutically acceptable mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprilate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

Preferred compounds of this invention are those compounds of formula I where X is

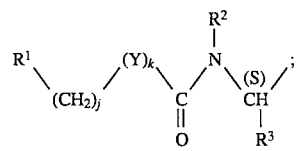

R is aryl, aryl($C_1$–$C_4$)alkyl or a structure having the formula —A—$(CH_2)_q$—$R^0$, where A is —S—;

q is 0;

R is aryl;

$R^1$ is aryl or unsaturated heterocycle;

j is 0, 1 or 2;

Y is —O— or —N($R^2$)—;

k is 1;

$R^2$ is hydrogen or methyl;

$R^3$ is an amino acid side chain, —$CH_2CH_3$, —$CH_2CH_2CH_3$, —$CH_2(CH_2)_2CH_3$, —$C(CH_3)_3$ or a structure having the formula, —$CH_2$—C(O)—$NR^2$—$(CH_2)_r$—$R^5$, where r is 0, 1, 2 or 3; and $R^5$ is cycloalkyl, aryl, heterocycle or unsaturated heterocycle;

or a pharmaceutically acceptable salt thereof.

Of these compounds, more preferred compounds are those where:

R is phenyl, phenylthio, naphthyl, naphthylthio, phenylethyl or naphthylethyl;
$R^1$ is phenyl, naphthyl or quinolinyl;
j is 1;
$R^2$ is hydrogen;
$R^3$ is an amino acid side chain, —$CH_2CH_3$ or a structure having the formula, —$CH_2$—C(O)—$NR^2$—$(CH_2)_r$—$R^5$, where
  r is 0, 1, 2 or 3; and
  $R^5$ is aryl or unsaturated heterocycle;
or a pharmaceutically acceptable salt thereof.

The most preferred compounds are those compounds of formula I where:
R is phenyl or phenylethyl;
$R^1$ is phenyl or quinolinyl; and
$R^3$ is —$CH_2CH_3$ or —$CH(CH_3)_2$;
or a pharmaceutically acceptable salt thereof.

The compounds of the formula I can be prepared using chemical synthetic methods well-known to one skilled in the art. For example, a preferred procedure used to prepare the compounds of formula I involves reacting an appropriately substituted oxirane of formula Ia in the presence of a base, or an oxirane of formula Ib, with a suitably substituted carboxylic acid compound, in an aprotic solvent in the presence of a coupling agent. The preferred oxirane reagent is that of formula Ib. The reaction is represented by the following reaction scheme I:

Reaction Scheme I:

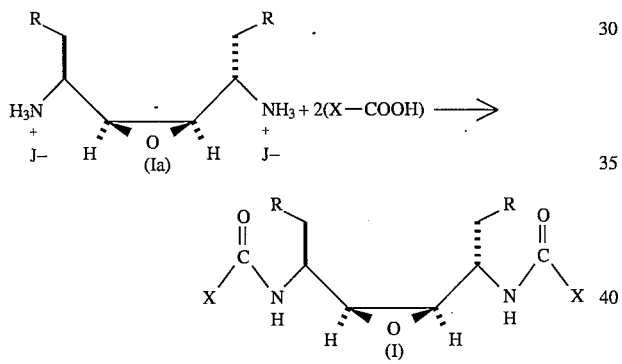

where R, X and J are as defined supra.

The above reaction can be carried out in the presence or absence of a catalyst but a catalyst is preferable. The preferred catalyst is hydroxybenzotriazole hydrate (HOBT.H₂O). Typical examples of coupling reagents include the carbodiimides such as N,N'-diethylcarbodiimide, dicyclohexylcarbodiimide (DCC); the imidazoles such as carbonyldiimidazole; as well as reagents such as 1-hydroxybenzotriazole mesylate, N-ethoxycarbonyl-2-ethoxy-1,2-dihydroquinoline (EEDQ), benzotriazol-1-yloxytris-(dimethylamino)phosphonium hexafluorophosphate (BOP), (o-benzotriaza-1-yl-N,N,N',N'-tetramethyluranium hexafluorophosphate (HBTU) and benzotriazol-1-yl-oxytripyrrolidinophosphonium hexafluorophosphate (PyBOP).

The carboxylic acid reactant is generally employed in an amount ranging from about equimolar proportions to about a three molar excess relative to the oxirane reactant, preferably in about a two molar excess. The coupling reagent is generally employed in an amount ranging from about equimolar proportions to a slight excess relative to the carboxylic acid reactant. Typical solvents suitable for use in this process include dimethylformamide or tetrahydrofuran. Solvent choice is not critical so long as the solvent employed is inert to the ongoing reaction and the reactants are sufficiently solubilized to effect the desired reaction. The reaction is generally substantially complete after about 1 to 72 hours when conducted at a temperature in the range of from about −15° C. to the reflux temperature of the reaction mixture. The reaction is preferably conducted at a temperature in the range of from about 0° C. to about 30° C. for about 24 to 48 hours. The reaction affords the compounds of formula I.

Once the reaction is complete, the product may be isolated by procedures well-known in the art, for example, filtration, or the reaction solvent may be removed by extraction, evaporation or decantation. The product may be further purified, if desired, by common techniques such as crystallization or chromatography over solid supports such as silica gel or alumina.

Compounds of the formula Ia

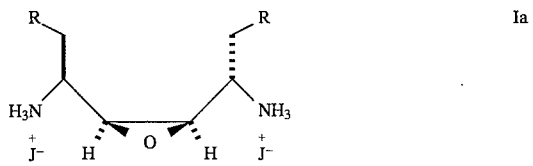

where:
R and J are as defined above;
are useful, as described supra, for making the compounds of formula I. Compounds of the formula Ia may be prepared by the following reaction scheme II:

Reaction Scheme II:

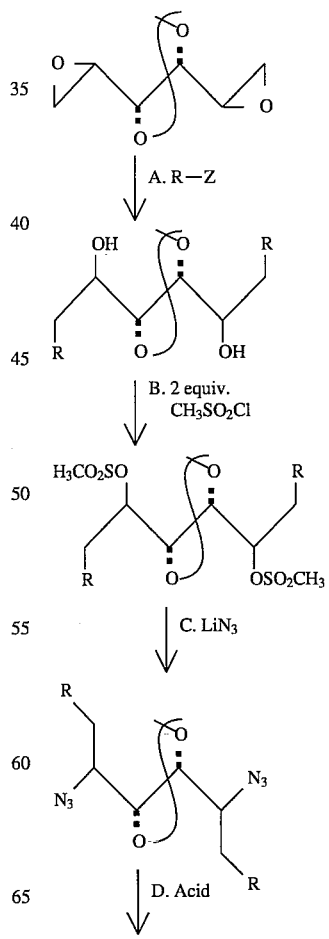

-continued
Reaction Scheme II:

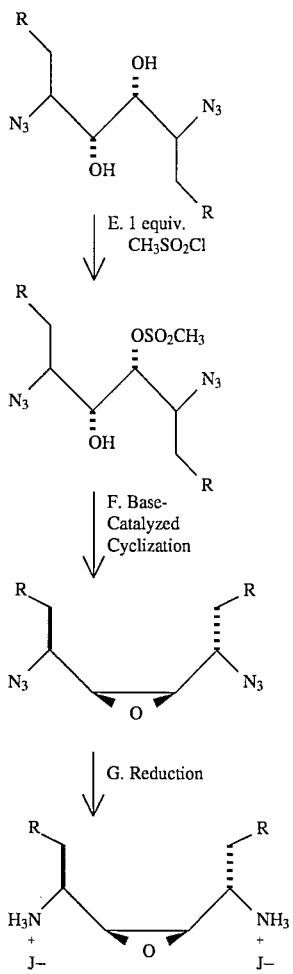

where R and J are as defined supra.

Reaction scheme II, supra, is accomplished by carrying out reactions A–G in sequential order. Once a reaction is complete, the intermediate compound may be isolated by procedures well-known in the art, for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme. Reaction scheme II is exemplified in Preparations 1–5 infra.

In reaction A, the reaction is carried out by combining 2,2-dimethyl-4,5-dioxirane-1,3-dioxolane with a nucleophilic reagent (R-Z) where Z is magnesium halide, lithium or ammonium, preferably magnesium bromide, in a mutual inert solvent. Better results may be obtained by catalysis with copper salts, for example copper (I) iodide or copper (I) bromide. The nucleophilic reagent is generally employed in an amount ranging from about equimolar proportions to about a 2 molar excess relative to the oxirane reactant, preferably in about a 0.5 molar excess. Typical solvents suitable for use in this reaction include any organic solvent such as diethyl ether or tetrahydrofuran. Solvent choice is not critical so long as the solvent employed is inert to the ongoing reaction and the reactants are sufficiently solubilized to effect the desired reaction. The reaction is generally substantially complete after about 1 to 24 hours when conducted at a temperature in the range of from about −40° C. to about 10° C. The reaction is preferably conducted at a temperature in the range of from about −5° C. to about 5° C. for about 2 to 6 hours.

In reaction B, the reaction is carried out by combining the compound isolated from reaction A, with methanesulfonyl chloride in a mutual inert solvent. The methanesulfonyl chloride is generally employed in an amount ranging from about equimolar proportions to about a three molar excess of the methanesulfonyl chloride reactant, preferably in about a two molar excess. A base, for example 2,6-lutidine or a trialkylamine such as triethylamine or diisopropylethylamine and the like, may optionally, be added to promote the reaction. Preferred bases for this reaction are the trialkylamines, especially triethylamine. Typical solvents suitable for use in this reaction include any organic solvent, preferably aprotic solvents, such as methylene chloride or chloroform. Solvent choice is not critical so long as the solvent employed is inert to the ongoing reaction and the reactants are sufficiently solubilized to effect the desired reaction. The reaction is generally substantially complete after about 15 minutes to 24 hours when conducted at a temperature in the range of from about 0° C. to the reflux temperature of the reaction mixture. The reaction is preferably conducted at a temperature in the range of from about 15° C. to about 30° C. for about 15 minutes to 4 hours.

In reaction C, the reaction is carried out by combining the compound, isolated from reaction B, with azide ion in a mutual inert solvent. The azide ion may be obtained for use in this reaction from inorganic salts, such as the alkali metal azides, for example lithium azide or from organic salts such as tetramethylguanidinium azide. The azide ion is generally employed in an amount ranging from about equimolar proportions to about a three molar excess of the azide ion, preferably in about a two molar excess. An improved yield may be obtained by the addition of a base, such as 2,6-lutidine. Typical solvents suitable for use in this process include any organic solvent such as hexamethylphosphoric triamide (HMPA), dimethylformamide or N,N'-dimethylpropyleneurea (DMPU). Solvent choice is not critical so long as the solvent employed is inert to the ongoing reaction and the reactants are sufficiently solubilized to effect the desired reaction. The reaction is generally substantially complete after about 1 to 24 hours when conducted at a temperature in the range of from about 0° C. to the reflux temperature of the reaction mixture. The reaction is preferably conducted at a temperature in the range of from about 25° C. to about 100° C. for about 4 to 12 hours.

In reaction D, the reaction is carried out by combining the compound isolated from reaction C, with a strong acid in an alcoholic solvent, such as methanol or ethanol. Typical acids suitable for use in this reaction include hydrohalic acids such as hydrochloric acid or hydrobromic acid, sulfuric acid and the like. Preferred acids are the hydrohalic acids, especially hydrochloric acid. The acid is generally employed in a large excess, for example in an amount ranging from about a ten molar excess to about a twenty molar excess of the acid reactant. The reaction is generally substantially complete after about 1 to 24 hours when conducted at a temperature in the range of from about 0° C. to about 40° C. The reaction is preferably conducted at a temperature in the range of from about 20° C. to about 30° C. for about 2 to 4 hours.

In reaction E, the reaction is carried out in a substantially similar manner as that described in reaction B, using methanesulfonyl chloride and the compound isolated from reaction D. However, the compound isolated from reaction D is generally employed in an amount ranging from about equimolar proportions to about a one molar excess relative to the methanesulfonyl chloride reactant.

In reaction F, the formation of the oxirane ring is carried out by base-catalyzed cyclization, preferably by combining the compound isolated from reaction E with alkoxide ion, in an appropriate solvent. The alkoxide ion is obtained from ammonium or alkali metal alkoxides and the like. Preferred alkoxide ions for this reaction are sodium methoxide and potassium methoxide. Typical solvents suitable for use in this process include any organic solvent such as methanol or tetrahydrofuran. The reaction is generally substantially complete after about 1 to 12 hours when conducted at a temperature in the range of from about 0° C. to about 40° C. The reaction is preferably conducted at a temperature in the range of from about 20° C. to about 30° C. for about 1 to 2 hours.

In reaction G, the reduction of the azido substituent to the corresponding amine is preferably carried out by catalytic hydrogenation, preferably by combining the compound isolated from reaction F with hydrogen gas in the presence of acetic acid and a palladium on carbon catalyst. Typical solvents suitable for use in this reaction include any organic solvent such as ethyl acetate. Solvent choice is not critical so long as the solvent employed is inert to the ongoing reaction and the azido reactant is sufficiently solubilized to effect the desired reaction. The reaction is generally substantially complete after about 1 to 24 hours when conducted at a temperature in the range of from about 0° C. to about 40° C. The reaction is preferably conducted at a temperature in the range of from about 20° C. to about 30° C. for about 2 to 5 hours.

Alternatively, the reduction of the azido substituent to the corresponding amine may be carried out by combining the compound isolated from reaction F with trialkyl- or triarylphosphine, in the presence of aqueous acetic acid. The preferred phosphine reactant is tributylphosphine. Typical organic solvents suitable for use in this reaction include mixtures such as ethyl acetate/acetonitrile containing 10% water. The reaction is generally substantially complete after about 1 to 12 hours when conducted at a temperature in the range of from about 0° C. to about 40° C. The reaction is preferably conducted at a temperature in the range of from about 20° C. to about 30° C. for about 0.5 to 2 hours.

Compounds of the formula X—COOH, where X is as defined supra, may be prepared by the following reaction scheme III:

Reaction Scheme III:

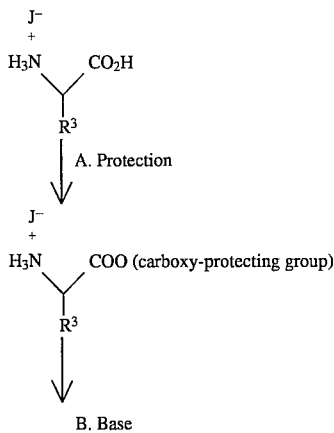

-continued
Reaction Scheme III:

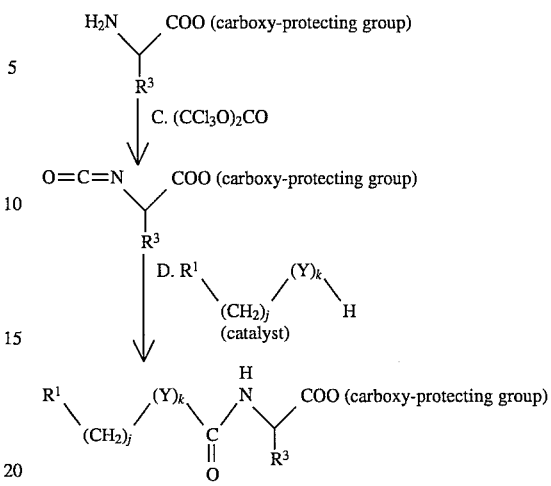

where J-, $R^3$, $R^1$, j, k, and Y are as defined supra.

Reaction scheme III, supra, is accomplished by carrying out reactions A–D in sequential order. Once a reaction is complete, the intermediate compound may be isolated by procedures well-known in the art, for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme. Reaction scheme III is exemplified in Preparations 6 and 7 infra.

In reaction A, the carboxy group on an suitably substituted 2-amino carboxylic acid compound is protected using a standard carboxy-protecting group, for example, by simply combining diphenyldiazomethane with the 2-amino carboxylic acid compound. The 2-amino carboxylic acid is typically utilized in the form of a salt, for example p-toluenesulfonic acid salt, such that the anion associated with the ammonic moiety is inert to the ongoing reaction. The diphenyldiazomethane is generally employed in an amount ranging from equimolar proportions to about a three molar excess, preferably in about a two molar excess. Typical solvents suitable for use in this reaction include any organic solvent such as acetonitrile. Solvent choice is not critical so long as the solvent employed is inert to the ongoing reaction and the reactants are sufficiently solubilized to effect the desired reaction. The reaction is generally substantially complete after about 15 minutes to 3 hours when conducted at a temperature in the range of from about 10° C. to about 40° C. The reaction is preferably conducted at a temperature in the range of from about 20° C. to about 30° C. for about 15 minutes to 4 hours.

In reaction B, the ammonic moiety is transformed to the corresponding amine by simply combining the compound isolated from reaction A with a base, for example bicarbonate, in water. The bicarbonate ion may be obtained for use in this process from inorganic salts, such as the alkali metal bicarbonates, for example lithium bicarbonate or sodium bicarbonate. The product was typically extracted from the reaction mixture using any organic solvent such as methylene chloride. The reaction is generally substantially complete after about 15 minutes to 3 hours when conducted at a temperature in the range of from about 20° C. to about 40° C. The reaction is preferably conducted at a temperature in the range of from about 15° C. to about 30° C. for about 15 minutes to 2 hours.

In reaction C, the reaction is carried out by simply combining the compound isolated from reaction B, with triphosgene in a mutual inert solvent. The compound isolated from reaction B is generally employed in an amount ranging from about equimolar proportions to about a two molar excess, preferably in about a one molar excess. A base, for example a trialkylamine such as triethylamine or diisopropylethylamine and the like, is added to promote the reaction. Typical solvents suitable for use in this reaction include any organic solvent such as toluene. Solvent choice is not critical so long as the solvent employed is inert to the ongoing reaction and the reactants are sufficiently solubilized to effect the desired reaction. The reaction is generally substantially complete after about 6 to 24 hours when conducted at a temperature in the range of from about 25° C. to the reflux temperature of the reaction mixture. The reaction is preferably conducted at a temperature in the range of from about 80° C. to the reflux temperature of the reaction mixture for about 8 hours to 12 hours.

In reaction D, the reaction is carried out by simply combining the compound isolated from reaction C with a compound of the formula, $$R^1-(CH_2)_j-(Y)_k-H$$

where $R^1$, j, k and Y are as defined above, provided that when Y is $-N(R^2)-$, $R^2$ must be hydrogen, in a mutual inert solvent. Better results may be obtained by catalysis with copper salts, for example copper (I) iodide or copper (I) chloride. The compound isolated from reaction C is generally employed in an amount ranging from about equimolar proportions to about a one molar excess. Typical solvents suitable for use in this reaction include any organic solvent such as dimethylformamide. Solvent choice is not critical so long as the solvent employed is inert to the ongoing reaction and the reactants are sufficiently solubilized to effect the desired reaction. The reaction is generally substantially complete after about 15 minutes to 3 hours when conducted at a temperature in the range of from about 10° C. to about 40° C. The reaction is preferably conducted at a temperature in the range of from about 15° C. to about 30° C. for about 15 minutes to 2 hours.

The carboxy group on the compound isolated from reaction D may be deprotected by hydrolysis of the ester to the corresponding carboxylic acid. The reaction is carried out by simply combining the compound isolated from reaction D with a strong acid in a mutual inert solvent. Typical solvents suitable for use in this reaction include any organic solvent such as dioxane. Solvent choice is not critical so long as the solvent employed is inert to the ongoing reaction and the reactants are sufficiently solubilized to effect the desired reaction. The reaction is generally substantially complete after about 15 minutes to 4 hours when conducted at a temperature in the range of from about 25° C. to the reflux temperature of the reaction mixture. The reaction is preferably conducted at a temperature in the range of from about 60° C. to about 100° C. for about 15 minutes to 1 hour.

Alternatively the carboxy group may be deprotected using catalytic hydrogenation, preferably by combining the compound isolated form reaction A with ammonium formate and palladium on carbon catalyst in an alcoholic solvent, such as methanol or ethanol. The reaction is generally substantially complete after about 1 to 4 hours when conducted at a temperature in the range of from about 0° C. to the reflux temperature of the reaction mixture. The reaction is preferably conducted at reflux temperature for about 2 to 5 hours.

Compounds of the formula X—COOH, where X is as defined supra, and particularly where $R^2$ is $C_1-C_4$ alkyl, may also be prepared by the following reaction scheme IV:

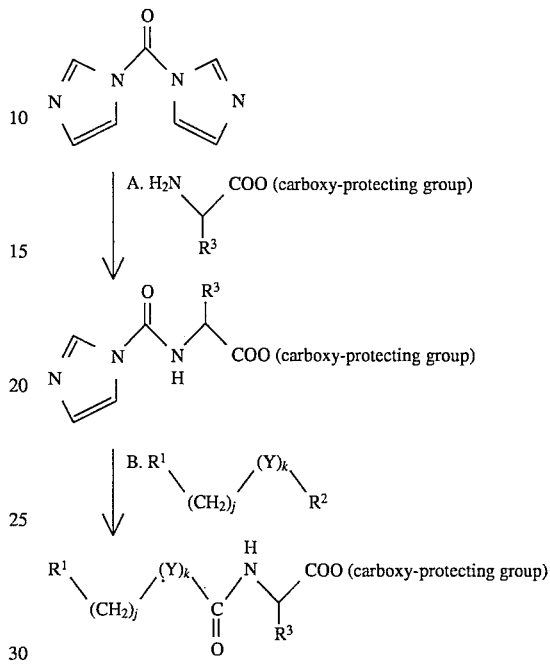

Reaction scheme IV, supra, is accomplished by carrying out reactions A and B in consecutive order. Once a reaction is complete, the product may be isolated by procedures well-known in the art, for example, the product may be crystallized and then collected by filtration, or the reaction solvent may be removed by extraction, evaporation or decantation. The product may be further purified, if desired, by common techniques such as crystallization or chromatography over solid supports such as silica gel or alumina, before carrying out the next step of the reaction scheme. Reaction scheme IV is exemplified in Preparations 8 and 9 infra.

In reaction A, the reaction is carried out by combining the compound isolated from reaction B, reaction scheme III with 1,1'-carbonyldiimidazole in a mutual inert solvent. The 1,1'-carbonyldiimidazole is generally employed in an amount ranging from about equimolar proportions to about a two molar excess of the carbonyldiimidazole reactant, preferably in about equimolar proportions. Typical solvents suitable for use in this reaction include any standard organic solvent such as acetonitrile. Solvent choice is not critical so long as the solvent employed is inert to the ongoing reaction and the reactants are sufficiently solubilized to effect the desired reaction. The reaction is generally substantially complete after about 15 minutes to 2 hours when conducted at a temperature in the range of from about 15° C. to 30° C. The reaction is preferably conducted at a temperature in the range of from about 20° C. to about 25° C. for about 15 minutes to 1 hour.

In reaction B, the reaction is carried out by combining the compound isolated from reaction C with a compound of the formula, $$R^1-(CH_2)_j-(Y)_k-H$$

where $R^1$, j, k and Y are as defined above, in a mutual inert solvent. The compound isolated from reaction A is generally employed in an amount ranging from about equimolar proportions to about a one molar excess. Typical solvents suitable for use in this reaction include any organic solvent such as acetonitrile. Solvent choice is not critical so long as the solvent employed is inert to the ongoing reaction and the reactants are sufficiently solubilized to effect the desired reaction. The reaction is generally substantially complete after about 30 minutes to 6 hours when conducted at a temperature in the range of from about 10° C. to about 40° C. The reaction is preferably conducted at a temperature in the range of from about 15° C. to about 30° C. for about 1 minutes to 4 hours.

The carboxy group on the compound isolated from reaction B may be deprotected by the methods described supra.

As noted supra, the optically active enantiomers of the compounds of formula I are considered part of this invention. Such optically active isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., "Enantiomers, Racemates, and Resolutions," John Wiley & Sons 1981

The compounds employed as initial starting material in the synthesis of the compounds of this invention are well-known and, to the extent not commercially available are readily synthesized by standard procedures commonly employed by those of ordinary skill in the art.

The pharmaceutically acceptable salts of the invention are typically formed by reacting a compound of formula I with an equimolar or excess amount of acid or base. The reactants are generally combined in a mutual solvent such as diethyl ether or benzene, for acid addition salts, or water or alcohols for base addition salts. The salts normally precipitate out of solution within about one hour to about ten days and can be isolated by filtration or other conventional methods.

The following Preparations and Examples further illustrate specific aspects of the present invention. It is to be understood, however, that these examples are included for illustrative purposes only and are not intended to limit the scope of the invention in any respect and should not be so construed.

In the following Preparations and Examples, the terms melting point, proton nuclear magnetic resonance spectra, mass spectra, infrared spectra, ultraviolet spectra, elemental analysis, high performance liquid chromatography, and thin layer chromatography are abbreviated "m.p.", "NMR", "MS", "IR", "UV", "Analysis", "HPLC", and "TLC", respectively. In addition, the absorption maxima listed for the IR spectra are only those of interest and not all of the maxima observed.

In conjunction with the NMR spectra, the following abbreviations are used: "s" is singlet, "d" is doublet, "dd" is doublet of doublets, "t" is triplet, "q" is quartet, "m" is multiplet, "dm" is a doublet of multiplets and "br.s", "br.d", "br.t", and "br.m" are broad singlet, doublet, triplet, and multiplet respectively. "J" indicates the coupling constant in Hertz (Hz). Unless otherwise noted, NMR data refers to the free base of the subject compound.

The nuclear magnetic resonance spectra were obtained on a Varian Associates EM-390 90 MHz or T-60 60 MHz instrument, on a Jeol FX-90Q 90 MHz instrument, on a Brüker Corp. 270 MHz instrument or on a General Electric QE-300 300 MHz instrument. The chemical shifts are expressed in delta ($\delta$) values (parts per million downfield from tetramethylsilane). The mass spectra were taken on a Varion-MAT 731 Spectrometer using carbon dendrite emitters. Infrared spectra were obtained on a Perkin-Elmer 281 instrument. Ultraviolet spectra were obtained on a Cary 118 instrument. Thin layer chromatography was carried out on E. Merck silica gel plates. Melting points are uncorrected.

PREPARATION 1

A. 2,2-Dimethyl-4(R),5(R)-bis(1(R)-hydroxy-2-phenylethyl)-1,3-dioxolane

A solution of 14.6 mL (43.8 mmol) of phenylmagnesium bromide in 24.6 mL of diethyl ether was added to a cold (–40° C.) solution of 0.278 g (1.46 mmol) of copper (I) iodide in 2 mL of dimethylsulfide and 22 mL of tetrahydrofuran, under nitrogen. After allowing this solution to stir for 5–10 minutes, a solution of 2.72 g (14.6 mmol) of 1,2:5,6-dianhydro-3,4-o-isopropylidene-D-mannitol in 12 mL of tetrahydrofuran was added. The reaction mixture was then warmed to 0° C. and allowed to react for 2 hours and 15 minutes, at which time a saturated ammonium chloride solution was slowly added. The resulting solution was vigorously stirred for 5 minutes and then transferred to a separatory funnel containing a 2:1 mixture of diethyl ether and water. The resulting layers were separated and the organic layer was reduced to dryness under reduced pressure. The resultant material was then purified using column chromatography (eluted with 2.5% acetone in methylene chloride). The fractions containing the desired product were combined and reduced to dryness under reduced pressure to provide 4.07 g of the desired subtitled intermediate as an oil.

NMR (CDCl$_3$): $\delta$ 7.35 (m, 10); 3.78 (m, 4); 3.15 (dd, 2); 2.90 (d, 2); 2.70 (m, 2); 1.45 (s, 6). MS: m/e 342 (M$^+$).

B. 2,2-Dimethyl-4(R),5(R)-bis(1(R)-methanesulfonyloxy-2-phenylethyl)-1,3-dioxolane A solution of 2.97 mL (38.3 mmol) of methanesulfonyl chloride in 20 mL of methylene chloride was added to a cold (0° C.) solution of 5.47 mL (39.3 mmol) of triethylamine and 6.4 g (18.7 mmol) of the subtitled intermediate of Preparation 1A, in 20 mL of methylene chloride. The reaction mixture was then warmed to room temperature. When the reaction was complete, as determined by thin layer chromatography (TLC), the reaction mixture was poured into a solution of 50 mL of 0.2N hydrochloric acid and 150 mL of diethyl ether. The resulting layers were separated and the organic layer was washed with a saturated sodium bicarbonate solution and then reduced to dryness under reduced pressure. The resultant material was then purified using column chromatography (eluted with 1:1 diethyl ether/hexane solution). The fractions containing the desired product were combined and reduced to dryness under reduced pressure to provide 3.7 g of the desired subtitled intermediate.

NMR (CDCl$_3$): $\delta$ 7.30 (m, 10); 4.88 (m, 2); 4.25 (d, 2); 3.10 (m, 4); 2.32 (s, 6); 1.52 (s, 6). MS: m/e 499 (M$^+$+1).

C. 2,2-Dimethyl-4(R),5(R)-bis(1(S)-azido-2-phenylethyl)-1,3-dioxolane

A solution of 0.784 g (16.0 mmol) of lithium azide, 4.0 g (14.6 mmol) of 18-crown-6 and 1.7 mL (14.6 mmol) of 2,6-lutidine was added to 3.6 g (7.2 mmol) of the subtitled intermediate of Preparation 1B, in 25 mL of N,N'-dimethylpropyleneurea. The reaction mixture was then heated to 95°–100° C. and allowed to react for approximately 7 hours.

When the reaction was complete, as determined by TLC, the reaction mixture was poured into 200 mL of a 1:1 mixture of 0.1N hydrochloric acid and diethyl ether. The resulting layers were separated and the organic layer was dried with sodium sulfate and then reduced to dryness under reduced pressure to provide 2.8 g of an oil. This oil was purified using column chromatography (eluted with a gradient eluent of 5–10% methylene chloride in toluene). The fractions containing the desired product were combined and reduced to dryness under reduced pressure to provide 1.03 g of the desired subtitled intermediate.

NMR (CDCl$_3$): δ 7.30 (m, 10); 4.12 (s, 2); 3.22 (t, 2); 3.05 (m, 4); 1.55 (s, 6).

D. 1,6-Diphenyl-2(S),5(S)-diazido-3(R),4(R)-dihydroxyhexane

To a solution of 0.370 g (0.943 mmol) of the subtitled intermediate of Preparation 1C in 4 mL of methanol, was slowly added 1.26 mL of 12M hydrochloric acid over a period of 3 hours. When the reaction was complete, as determined by TLC, the reaction mixture was diluted with 10 mL of acetonitrile and concentrated two times. The resultant material was redissolved in ethyl acetate and washed with a half-saturated solution of sodium bicarbonate. The resulting layers were separated and the organic layer was then reduced to dryness under reduced pressure to provide an oil. This oil was purified using column chromatography (eluted with a gradient eluent of 0–20% ethyl acetate in methylene chloride). The fractions containing the desired product were combined, reduced to dryness under reduced pressure and then recrystallized from a solution of diethyl ether and hexane to provide 0.309 g of the desired subtitled intermediate.

NMR (CDCl$_3$): δ 7.25 (m, 10); 3.60 (m, 4); 3.0 (m, 4); 2.65 (d, 2). MS: m/e 353 (M$^+$+1). Analysis for C$_{18}$H$_{20}$N$_6$O$_2$: Calc.: C, 61.35; H, 5.72; N, 23.85; Found: C, 61.15; H, 5.73; N, 23.70.

E. 1,6-Diphenyl-2(S),5(S)-diazido-3(R)-methansulfonyloxy-4(R)-hydroxyhexane

A solution of 13.5 µL (0.170 mmol) of methanesulfonyl chloride in 300 µL of methylene chloride was slowly added to a cold (0° C.) solution of 80 mg (0.23 mmol) of the subtitled intermediate of Preparation 1D and 32 µL (0.23 mmol) of triethylamine in 0.6 mL of methylene chloride. The reaction mixture was warmed to room temperature, allowed-to react for 15 minutes and then poured into 50 mL of a 3:2 mixture of diethyl ether and 0.1N hydrochloric acid. The resulting layers were separated and the organic layer was washed with a half-saturated sodium bicarbonate solution and then reduced to dryness under reduced pressure to provide a foam. This foam was purified using column chromatography (eluted with a 1:2 ethyl acetate/methylene chloride solution). The fractions containing the desired product were combined and reduced to dryness under reduced pressure to provide 100 mg of a 60:40 mixture of the desired subtitled intermediate and the starting material, 1,6-diphenyl-2(S),5(S)-diazido-3(R),4(R)-dihydroxyhexane.

F. 1,6-Diphenyl-2(S),5(S)-diazido-3,4-cis-epoxyhexane

To a cold (0° C.) solution of 60 mg (0.14 mmol) of the subtitled intermediate of Preparation 1E in 1.5 mL of a 2:1 methanol/tetrahydrofuran solution, was added 0.325 mL of a methanolic solution of 0.5M sodium methoxide. The reaction mixture was then warmed to room temperature and allowed to react for one hour, followed by the addition of 3 mL of diethyl ether containing 2 drops of acetic acid. The resulting solution was then poured into a mixture of 25 mL of a saturated sodium bicarbonate solution and 40 mL of diethyl ether. The resulting layers were separated and the organic layer was reduced to dryness under reduced pressure to provide an oil. This oil was purified using column chromatography (eluted with 20% hexane in methylene chloride). The fractions containing the desired product were combined and reduced to dryness under reduced pressure to provide 31 mg of the desired subtitled intermediate.

NMR (CDCl$_3$): δ 7.30 (m, 10); 3.57 (m, 1); 3.45 (m, 1); 3.18 (m, 2); 2.94 (m, 4).

G. 1,6-Diphenyl-2(S),5(S)-diammonio-3,4-cis-epoxyhexane dihydrochloride

To a suspension of 350 mg of 5% palladium on carbon in 10 mL of a 9:1 ethyl acetate/acetic acid solution, was added 0.368 g (1.11 mmol) of the subtitled intermediate of Preparation 1F, above. The mixture was then stirred rapidly under hydrogen for approximately 3½ hours. When the reaction was complete, as determined by TLC, the mixture was diluted with ethyl acetate and the 5% palladium on carbon was removed by filtration. The filtrate was then cooled overnight to provide 0.325 g of 1,6-diphenyl-2(S),5(S)-diammonio-3,4-cis-epoxyhexane diacetate. To a solution of 0.100 g (0.249 mmol) of the diacetate in 4 mL of a 1:1 methylene chloride/diethyl ether solution, was slowly added 0.498 mL of a 1N hydrochloric acid in acetonitrile resulting in the formation of a white solid. This solid was isolated by centrifugation to provide 0.090 g of the desired subtitled product.

NMR (d$_6$-DMSO): δ 8.40 (br.s, 6); 7.30 (m, 10); 3.40 (m, 4); 3.05 (m, 4). MS: m/e 284 (M$^+$ −2Cl).

PREPARATION 2

A. 2,2-Dimethyl-4(R),5(R)-bis(1(R)-hydroxy-2-naphth-2-yl-ethyl)-1,3-dioxolane The desired subtitled intermediate was prepared substantially in accordance with the procedure detailed in Preparation 1A using 27.29 mmol of 2-naphthylmagnesium bromide, 183 mg of copper (I) iodide, 1.30 mL (17.70 mmol) of dimethylsulfide and 1.502 g (8.07 mmol) of 1,2:5,6-dianhydro-3,4-o-isopropylidene-D-mannitol in approximately 58 mL of tetrahydrofuran to provide 2.81 g of a white solid.

NMR (CDCl$_3$): δ 7.78 (m, 8); 7.43 (m, 6); 3.90 (m, 2); 3.81 (m, 2); 3.32 (dd, 2); 2.90 (dd, 2); 2.81.(br.s, 2); 1.53 (s, 6). MS: m/e 442 (H$^+$). Analysis for C$_{29}$H$_{30}$O$_4$: Calc.: C, 78.71; H, 6.83; Found: C, 78.44; H, 7.11.

B. 2,2-Dimethyl-4(R),5(R)-bis(1(R)-methanesulfonyloxy-2-naphth-2-yl-ethyl)-1,3-dioxolane The desired subtitled intermediate was prepared substantially in accordance with the procedure detailed in Preparation 1B using 2.40 mL (31.0 mmol) of methanesulfonyl chloride, 2.80 mL (20.1 mmol) of triethylamine and 2.81 g (6.35 mmol) of the subtitled intermediate of Preparation 2A to provide 3.02 g of a white solid.

NMR (CDCl$_3$): δ 7.80 (m, 8); 7.50 (m, 4); 7.36 (m, 2); 5.00 (m, 2); 4.35 (br.s, 2); 3.26 (m, 4); 2.27. (s, 6); 1.57 (s, 6). MS: m/e 598 (M$^+$). Analysis for C$_{31}$H$_{34}$O$_8$S$_2$: Calc.: C, 62.19; H, 5.72; Found: C, 62.00; H, 5.70.

C. 2,2-Dimethyl-4(R),5(R)-bis(1(S)-azido-2-naphth-2-yl-ethyl)-1,3-dioxolane

The desired subtitled intermediate was prepared substantially in accordance with the procedure detailed in Preparation 1C using 1.999 g (40.80 mmol) of lithium azide, 1.175 mL (10.09 mmol) of 2,6-lutidine and 3.00 g (5.01 mmol) of the subtitled intermediate of Preparation 2B to provide 946 mg of a viscous oil which contained 894 mg of the desired compound.

NMR (CDCl$_3$): δ 7.83 (m, 6); 7.70 (br.s, 2); 7.52 (m, 4); 7.35 (m, 2); 4.23 (s, 2); 3.39 (m, 2); 3.20. (m, 4); 1.59 (s, 6). MS: m/e 492 (M$^+$). Analysis for C$_{29}$H$_{28}$N$_6$O$_2$: Calc.: C, 70.71; H, 5.73; N, 17.06; Found: C, 70.77; H, 5.82; N, 16.82.

D. 1,6-Dinaphth-2-yl-2(S),5(S)-diazido-3(R),4(R)-dihydroxyhexane

The desired subtitled intermediate was prepared substantially in accordance with the procedure detailed in Preparation 1D using 41.9 mg (0.0851 mmol) of the subtitled intermediate of Preparation 2C and 4 drops of concentrated hydrochloric acid in 0.25 mL of a 2.5:1:6.5 acetic acid/water/tetrahydrofuran solution. The reaction solution was stirred at reflux for 17 hours to provide 28.7 mg of a white solid.

NMR (CDCl$_3$): δ 7.75 (m, 8); 7.50 (m, 4); 7.34 (m, 2); 3.70 (br.s, 4); 3.15 (m, 4); 2.48 (br.s, 2). MS: m/e 452 (M$^+$). Analysis for C$_{26}$H$_{24}$N$_6$O$_2$: Calc.: C, 69.01; H, 5.35; N, 18.57; Found: C, 69.15; H, 5.37; N, 18.37.

E. 1,6-Dinaphth-2-yl-2(S),5(S)-diazido-3(R)-methanesulfonyloxy-4(R)-hydroxyhexane The desired subtitled intermediate was prepared substantially in accordance with the procedure detailed in Preparation 1E using 40 μL (0.52 mmol) of methanesulfonyl chloride, 697 mg (1.54 mmol) of the subtitled intermediate of Preparation 2D and 0.212 mL (1.52 mmol) of triethylamine to provide a solid, which was used without further purification.

F. 1,6-Dinaphth-2-yl-2(S),5(S)-diazido-3,4-cis-epoxyhexane

The desired subtitled intermediate was prepared substantially in accordance with the procedure detailed in Preparation 1F using the subtitled intermediate of Preparation 2E and 4. 50 mL of 0.5M sodium methoxide in methanol, to provide 261 mg of a white solid.

NMR (CDCl$_3$): δ 7.80 (m, 8); 7.44 (m, 6); 3.73 (m, 1); 3.62 (m, 1); 3.34 (dd, 1); 3.23 (dd, 1); 3.11 (m, 4). MS: m/e 434 (M$^+$). Analysis for C$_{26}$H$_{22}$N$_6$O: Calc.: C, 71.87; H, 5.10; N, 19.34; Found: C, 72.09; H, 5.29; N, 19.32.

G. 1,6-Dinaphth-2-yl-2(S),5(S)-diammonio-3,4-cis-epoxyhexane dihydrochloride The desired subtitled product was prepared substantially in accordance with the procedure detailed in Preparation 1G by combining 322 mg (0.741 mmol) of the subtitled intermediate of Preparation 2F and 330 mg of 5% palladium on carbon under hydrogen to provide 95.8 mg of the 1,6-dinaphth-2-yl-2(S),5(S)-diammonio-3,4-cis-epoxyhexane diacetate salt. The dihydrochloride salt was then prepared using the diacetate salt and 0.5 mL of a 1N hydrochloric acid in acetonitrile to provide 69.2 mg of a white solid.

NMR (d$_6$-DMSO): δ 8.53 (br.s, 3); 8.23 (br.s, 3); 3.90 (m, 8); 7.54 (m, 6); 3.05–3.85 (m, 8). MS: m/e 383 (M$^+$+1 −2Cl). Analysis for C$_{26}$H$_{28}$N$_2$OCl$_2$: Calc.: C, 68.57; H, 6.20; N, 6.15; Found: C, 68.48; H, 6.32; N, 6.32.

PREPARATION 3

A. 2,2-Dimethyl-4(R),5(R)-bis(1(R)-hydroxy-2-naphth-2-yl-thioethyl)-1,3-dioxolane To a solution of 1.172 g (6.29 mmol) of 2,2-dimethyl-4, 5-dioxirane-1,3-dioxolane in 64 mL of tetrahydrofuran was added 4.075 g (25.43 mmol) of 2-naphthylthiol. After the solid had completely dissolved, 2.20 mL (12.6 mmol) of di(isopropyl)ethylamine was added. The resulting solution was heated to reflux and allowed to react for approximately 24 hours. After cooling, the solution was transferred to a separatory funnel containing a methylene chloride and a saturated brine solution. The resulting layers were separated and the organic layer was reduced to dryness under reduced pressure. The resultant material was then purified using column chromatography (eluted with a 30% ethyl acetate/65% hexane/5% methylene chloride solution). The fractions containing the desired product were combined and reduced to dryness under reduced pressure to provide 2.88 g of the desired subtitled intermediate.

NMR (CDCl$_3$): δ 7.76 (m, 8); 7.44 (m, 6); 3.85 (m, 4); 3.72 (s, 2); 3.60 (dd, 2); 3.02 (dd, 2); 1.32 (s, 6). MS: m/e 506 (M$^+$). Analysis for C$_{29}$H$_{30}$O$_4$S$_2$: Calc.: C, 68.74; H, 6.90; Found: C, 69.03; H, 6.09.

B. 2,2-Dimethyl-4(R),5(R)-bis(1(R)-methanesulfonyloxy-2-naphth-2-yl-thioethyl)-1,3-dioxolane The desired subtitled intermediate was prepared substantially in accordance with the procedure detailed in Preparation 1B using 1.10 mL (14.2 mmol) of methanesulfonyl chloride, 2.12 mL (15.2 mmol) of triethylamine and 2.84 g (5.60 mmol) of the subtitled intermediate of Preparation 3A to provide 3.02 g of a solid.

C. 2,2-Dimethyl-4(R),5(R)-bis(1(S)-azido-2-naphth-2-yl-thioethyl)-1,3-dioxolane The desired subtitled intermediate was prepared substantially in accordance with the procedure detailed in Preparation 1C using 602 mg (12.3 mmol) of lithium azide, 1.40 mL (12.0 mmol) of 2,6-lutidine and subtitled intermediate of Preparation 3B to provide 539 mg of a colorless oil which was calculated to contain 894 mg of the desired compound.

NMR (CDCl$_3$): δ 7.91 (s, 1); 7.78 (m, 7); 7.49 (m, 6); 4.78 (s, 2); 3.73 (m, 4); 3.39 (m, 2); 1.56 (s, 6). MS: m/e 556 (M$^+$).

D. 1,6-Dinaphth-2-ylthio-2(S),5(S)-diazido-3(R),4(R)-dihydroxyhexane

The desired subtitled intermediate was prepared substantially in accordance with the procedure detailed in Preparation 2D using 1.24 g (2.23 mmol) of the subtitled intermediate of Preparation 3C and 0.5 mL of concentrated hydrochloric acid in 15.2 mL of a 3:1:7.7 acetic acid/water/tetrahydrofuran solution. The reaction solution was stirred at reflux for 3 hours to provide 937 mg of a white solid.

NMR (CDCl$_3$): δ 7.79 (m, 8); 7.46 (m, 6); 4.23 (br.s, 2); 3.72 (m, 2); 3.60 (m, 2); 3.37 (m, 2); 3.02 (d, 2). MS: m/e 516 (M$^+$). Analysis for C$_{26}$H$_{24}$N$_6$O$_2$S$_2$: Calc.: C, 60.44; H, 4.68; N, 16.27; Found: C, 60.39; H, 4.85; N, 15.97.

E. 1,6-Dinaphth-2-ylthio-2(S),5(S)-diazido-3(R)-methanesulfonyloxy-4(R)-hydroxyhexane The desired subtitled intermediate was prepared substantially in accordance with the procedure detailed in Preparation 1E using 23.7 μL (0.306 mmol) of methanesulfonyl chloride, 211 mg (408 mmol) of the subtitled intermediate of Preparation 3D and 0.60 mL (0.30 mmol) of triethylamine to provide a solid.

F. 1,6-Dinaphth-2-ylthio-2(S),5(S)-diazido-3,4-cis-epoxyhexane

The desired subtitled intermediate was prepared substantially in accordance with the procedure detailed in Preparation 1F using the subtitled intermediate of Preparation 3E and 0.70 mL of solution of 0.5M sodium methoxide in methanol, to provide 94 mg of a colorless oil.

NMR (CDCl$_3$): δ 8.03 (m, 2); 7.79 (m, 6); 7.52 (m, 6); 3.65 (m, 2); 3.43 (m, 2); 3.50 (dd, 1); 3.20 (dd, 1); 3.00 (m, 1). MS: m/e 498 (M$^+$). Analysis for C$_{26}$H$_{22}$N$_6$OS$_2$: Calc.: C, 62.63; H, 4.45; N, 16.85; Found: C, 62.88; H, 4.58; N, 16.73.

G. 1,6-dinaphth-2-ylthio-2(S),5(S)-diammonio-3,4-cis-epoxyhexane diacetate

To a solution of 172 mg (0.345 mmol) of the subtitled intermediate of Preparation 3F in a 6:4:1 ethyl acetate/acetonitrile/water mixture, was added 260 μL (1.04 mmol) of tri-n-butylphosphine and 60.0 μL of glacial acetic acid. The reaction mixture was allowed to react for approximately 30 minutes at room temperature and then concentrated under reduced pressure to provide an oil. This oil was recrystalized using an ethyl acetate/hexane solution to provide 12.4 mg of the desired titled intermediate as a white powder.

NMR (d$_6$-DMSO): δ 8.09 (s, 1); 7.95 (s, 1); 7.72–7.90 (m, 9); 7.38–7.62 (m, 9); 3.08–3.34 (m, 4); 2.53–2.95 (m, 4); 1.86 (s, 6). MS: m/e 446 (M$^+$ –2HOAc). Analysis for C$_{30}$H$_{34}$N$_2$O$_5$S$_2$: Calc.: C, 63.58; H, 6.05; N, 4.94; S, 11.32; Found: C, 63.74; H, 6.17; N, 4.85; S, 11.10.

PREPARATION 4

1,8-Diphenyl-3(S),6(S)-diammonio-4,5-cis-epoxyoctane hydrochloride

The desired subtitled product was prepared substantially in accordance with the procedure detailed in Preparation 1A–G.

NMR (d$_6$-DMSO) δ 8.35 (br.s, 6); 7.20 (m, 10); 3.30 (m, 3); 3.10 (m, 1); 2.70 (m, 4); 2.0 (m, 4).

PREPARATION 5

1,10-Diphenyl-4(S),7(S)-diammonio-5,6-cis-epoxydecane hydrochloride

The desired subtitled product was prepared substantially in accordance with the procedure detailed in Preparation 1A–G.

NMR (d$_6$-DMSO) δ 8.35 (br.s, 6); 7.35 (m, 10); 3.45 (m, 3); 3.35 (m, 1); 3.05 (m, 4); 1.8 (m, 8).

PREPARATION 6

A. Benzhydryl 2(S)-ammonio-3(S)-methylpentanoate, p-toluenesulfonate

Diphenyldiazomethane was added to a solution of 15.03 g (49.54 mmol) of L-isoleucine, p-toluenesulfonate in 450 ml of a 4:5 acetonitrile/methanol solution until a light pink color persisted (17.12 g (88.16 mmol) of diphenyldiazomethane), at which time 2 mL of glacial acetic acid was added. The resultant solution was stirred for approximately 15 minutes at room temperature and then concentrated under reduced pressure to provide a yellow solid. This solid was then purified by recrystallization in hot acetonitrile to provide 21.64 g of the desired subtitled intermediate.

NMR (CD$_3$OD) δ 7.67 (d, J=9 Hz, 2); 7.37 (m, 10); 7.20 (d, J=9 Hz, 2); 6.98 (s, 1); 4.13 (d, J=3 Hz, 1); 2.34 (s, 3); 2.01 (m, 1); 1.17–1.46 (m, 2); 0.80–0.97 (m, 6).

B. Benzhydryl 2(S)-amino-3(S)-methylpentanoate

To a solution of 21.64 g (46.08 mmol) of the subtitled intermediate of Preparation 4A, was added 450 mL of a saturated sodium bicarbonate solution which resulted in the release of a gas. When the reaction was complete, the resultant layers were separated and the organic layer was reduced to dryness under reduced pressure to provide 13.61 g of the desired subtitled intermediate.

NMR (CDCl$_3$) δ 7.19–7.45 (m, 10); 7.93 ( s, 1); 3.47 (d, J=3 Hz, 1); 1.85 (m, 1); 1.33–1.50 (m, 4); 0.92 (d, J=8 Hz, 3); 0.83 (t, J=8, 3).

C. Benzhydryl 2(S)-carbamoyl-3(S)-methylpentanoate

A solution of 4.97 g (16.7 mmol) of the subtitled intermediate of Preparation 4B and 4.7 mL (33.7 mmol) of triethylamine was cannulated into a hot (60° C.) solution of 2.51 g (8.46 mmol) of triphosgene in 90 mL of toluene. The temperature was then increased to 100° C. and the solution was allowed to react overnight. The reaction mixture was cooled to 0° C. resulting in the formation of a precipitate. This precipitate was removed by filtration and washed with a 1:1 ethyl acetate/hexane solution. The resulting solution was reduced to dryness under reduced pressure to provide 5.45 g of the desired subtitled intermediate of sufficient purity (ca. 90% by NMR) for use in subsequent reactions.

NMR (CDCl$_3$) δ 7.23–7.47 (m, 10); 6.98 (s, 1); 4.05 (d, J=3 Hz, 1); 2.05 (m, 1); 1.18 (quintet, J=8 Hz, 2); 1.00 (d, J=8 Hz, 3); 0.80 (t, J=8 Hz, 3).

D. Benzhydryl 2(S)-N-[(quinol-2-ylmethoxy) carbonyl]amino-3(S)-methylpentanoate To a solution of 0.506 g (3.18 mmol of 2hydroxymethylquinoline and 0.315 g (3.18 mmol) of copper (I) chloride in anhydrous dimethylformamide, was added 1.13 g (3.50 mmol) of the subtitled intermediate of Preparation 4C. When the reaction was substantially complete, as indicated by TLC, the reaction mixture was diluted with ethyl acetate and washed with a half-saturated brine solution. The resulting layers were separated and the organic layer was dried over sodium sulfate and reduced to dryness under reduced pressure to provide a brown oil. This oil was purified by column chromatography (eluted with 65% hexane in ethyl acetate) to provide 1.23 g of the desired subtitled intermediate.

NMR (CDCl₃) δ 8.15 (d, 1); 8.05 (d, 1); 7.8 (d, 1); 7.70 (t, 1); 7.55 (t, 1); 7.45 (d, 1); 7.30 (m, 10); 6.92 (s, 1); 5.43 (d, 1); 5.40 (s, 2); 4.5 (m, 1); 2.0 (m, 1); 1.2 (m, 2); 0.9 (d, 3); 0.82 (t, 3).

E. 2(S)-N-[(Quinolin-2-ylmethoxy) carbonyl]amino-3(S)-methylpentanoic acid

The subtitled intermediate of Preparation 4C, above, was dissolved in 12 mL of dioxane containing 3 mL of concentrated hydrochloric acid. The resulting solution was heated to 100° C. and allowed to react for appproximately 5 minutes, then cooled to room temperature and stirred until the reaction was substantially complete, as indicated by TLC. The resulting solution was reduced to dryness under reduced pressure and then redissolved in an aqueous sodium bicarbonate solution. The resulting solution was washed with 100 mL of diethyl ether and then acidified to pH 4 using 1N hydrochloric acid. The desired product was then extracted with a solution of 10% isopropanol in methylene chloride, dried over sodium sulfate and filtered. The filtrate was then reduced to dryness under reduced pressure to provide 0.567 g of the desired titled product.

NMR (d₆-DMSO) δ 8.35 (d, 1); 7.92 (d, 2); 7.70 (m, 2); 7.53 (m, 2); 5.22 (s, 2); 3.92 (m, 1); 1.78 (m, 1); 1.40 (m, 1); 1.20 (m, 1); 0.90 (m, 6).

PREPARATION 7

A. Benzhydryl 2(S)-N-[[N(methyl)-N(pyrid-2-ylethyl) amino]carbonyl]amino-3(S)-methylpentanoate To a solution of 1.13 g (3.50 mmol) of the subtitled intermediate of Preparation 4C in 2 mL of methylene chloride, was added 0.441 mL (3.18 mmol) of N(pyrid-2-ylethyl)amine. When the reaction was complete, as indicated by TLC, the reaction solution was poured through a silica column (eluted with 5% methanol in ethyl acetate). The fractions containing the desired product were combined and reduced to dryness to provide 1.33 g of the desired subtitled intermediate.

NMR (CDCl₃) δ 8.43 d, 1); 7.55 (t, 1) 7.3 (m, 10); 7.10 (m, 2); 6.90 (s, 1) 5.63 (d, 1); 4.60 (m, 1); 3.65 (m, 2) 3.02 (t, 2); 2.81 (s, 3); 1.95 (m, 1) 1.3 (m, 1); 1.15 (m, 1); 0.85 (m, 6).

B. 2-(S)-N-[[N(Methyl)-N(pyrid-2-ylethyl) amino]carbonyl]amino-3(S)-methylpentanoic acid The desired subtitled product was prepared substantially in accordance with the procedure detailed in Preparation 4E using 1.1 g (2.39 mmol) of the subtitled intermediate of Preparation 5A and 3 mL of concentrated hydrochloric acid to provide 0.527 g of a solid.

NMR (CDCl₃) δ 10.00 (br.s, 1); 8.55 (d, 1); 7.62 (d, 1); 7.2 (m, 2); 5.7 (d, 1); 4.35 (m, 1); 3.70 (m, 2); 3.06 (t, 2); 2.83 (s, 3); 1.95 (m, 1); 1.50 (m, 1); 1.20 (m, 1); 0.9 (m, 6).

PREPARATION 8

A. Benzhydryl-2(S)-N(imidazol-1-ylcarbonyl)aminohexanoate

A solution of 400 mg (1.34 mmol) of benzhydryl-2-(S)-aminohexanoate in 3 mL of acetonitrile was added to 218 mg (1.34 mmol) of 1,1'-carbonyldiimidazolyl in 2 mL of acetonitrile. The resulting solution was stirred at room temperature for about 45 minutes and then purified using column chromatography (eluted with 25% ethyl acetate in methylene chloride) to provide 350 mg of the desired subtitled intermediate.

NMR (CDCl₃) δ 8.15 (s, 1); 7.35 (s, 10); 7.08 (s, 1); 6.95 (s, 1); 6.90 (d, 1); 4.80 (m, 1); 2.0 (m, 1); 1.80 (m, 1); 1.30 (m, 3); 1.15 (m, 3); 0.82 (t, 3).

B. Benzhydryl-2(S)-N-[[N(methyl)-N[(quinolin-2-ylmethyl)amino]carbonyl]]aminohexanoate A solution of 300 mg (0.766 mmol) of the subtitled intermediate of Preparation 6A in 1 mL of acetonitrile was added to 132 mg (0.766) of N(methyl)-2-aminoquinoline in 1 mL of acetonitrile. When the reaction was complete, as indicated by TLC, the reaction solution was reduced to dryness under reduced pressure to provide an oil. This oil was purified using column chromatography (gradient eluent of 10–30% ethyl acetate in methylene chloride). The fractions containing the desired product were combined and reduced to dryness under reduced pressure to provide 330 mg of the desired subtitled intermediate.

NMR (CDCl₃) δ 8.15 (d, 1); 8.0 (d, 1); 7.80 (d, 1); 7.70 (t, 1); 7.55 (t, 1); 7.40 (d, 1); 7.30 (s, 10); 6.90 (s, 1); 6.08 (br.s, 3); 4.70 (m, 3); 3.02 (s, 3); 1.90 (m, 1); 1.75 (m, 1); 1.20 (m, 4); 0.80 (t, 3).

C. 2(S)-N-[[N(Methyl)-N(quinolin-2-ylmethyl) amino]carbonyl]aminohexanoic acid To a solution of 330 mg (0.666 mmol) of the subtitled intermediate of Preparation 6B in 2 mL of methanol, were added 105 mg (1.66 mmol) of ammonium formate and 83 mg of 5% palladium on carbon. The reaction mixture was allowed to react at reflux temperature for approximately 2 hours. When the reaction was complete, as determined by TLC, the reaction mixture was cooled, diluted with ethyl acetate and the 5% palladium on carbon was removed by filtration. The solution was then combined with 50 mL of water, the resulting layers were then separated and the organic layer was reduced to dryness under reduced pressure to provide 165 mg of the desired subtitled product.

NMR (d₆-DMSO) δ 8.30 (d, 1); 7.92 (d, 2); 7.70 (t, 1); 7.55 (t, 2); 7.35 (d, 1); 6.60 (d, 1); 4.62 (s, 2); 4.03 (m, 1); 2.85 (s, 3); 1.62 (m, 2); 1.20 (m, 4); 0.80 (t, 3).

PREPARATION 9

A. Benzhydryl-2(S)-N-[(quinolin-2-ylmethoxy)carbonyl]aminohexanoate

A solution of 40 mg (0.10 mmol) of the subtitled intermediate of Preparation 6A in 1 mL of dimethylformamide was added to 16.5 mg (0.104 mmol) of 2-hydroxymethyl quinoline, 12.5 mg (0.102 mmol) of 4-dimethylaminopyridine and 0.10 mmol of copper (I) chloride in dimethylformamide. The resulting reaction mixture was allowed to react for approximately 3 hours at room temperature and then purified using column chromatography (eluted with 65% hexane in ethyl acetate) to provide 37 mg of the desired subtitled intermediate.

NMR (CDCl₃) δ 8.15 (d, 1); 8.05 d, 1); 7.80 (d, 1); 7.70 (t, 1); 7.55 t, 1); 7.45 (d, 1); 7.30 (s, 10); 6.90 (s, 1); 5.45 (d, 1); 5.40 (s, 2); 4.55 m, 1); 1.90 (m, 1); 1.72 (m, 1); 1.20 (m, 4); 0.80 (t, 3).

Example 1

1,6-Diphenyl-2(S),5(S)-di[N-[2(S)-N(benzyloxycarbonyl)amino-3-methyl-butanoyl]amino]-3,4-cis-epoxyhexane A solution of 215 mg (0.818 mmol) of 2(S)-N(benzyloxycarbonyl)amino-3-methylbutanoic acid, 12 mg (0.082 mmol) of hydroxybenzotriazole monohydrate (HOBT.H$_2$O), 104 μl (0.818 mmol) of N-methyl morpholine (NMM) and 362 mg (0.818 mmol) of benzotriazol-1-yloxytris(dimethylamino)phosphonium hexafluorophosphate (BOP) in 2 mL of dimethylformamide was prepared and allowed to stir at room temperature for approximately 10 min. Concurrently, 80 μL (0.40 mmol) of N,N-dicyclohexylamine was added to a solution of 71 mg (0.20 mmol) of the subtitled intermediate of Preparation 1G in 6 mL of dimethyl-formamide, resulting in the formation of a white solid. This solid was removed by centrifugation and the filtrate was added to the above solution. The resulting reaction mixture was concentrated under reduced pressure to a volume of 2.0 mL and allowed to react for about 48 hours at room temperature. The reaction mixture was then diluted with 20 mL of ethyl acetate and the resulting solution was added to 120 mL of a 2:1 ethyl acetate/0.1N hydrochloric acid solution. The resultant layers were separated and the organic layer was washed with a 1:1 saturated sodium bicarbonate/brine solution, dried with sodium sulfate, filtered and then reduced to dryness under reduced pressure to provide 110 mg of material. This material was then purified using flash chromatography (eluted with 65% toluene in ethyl acetate). The fractions containing the desired product were combined and reduced to dryness under reduced pressure to provide 52 mg of the desired titled product.

NMR (80% CDCl$_3$/20% CD$_3$OD): δ 7.35 (s, 10); 7.18 (m, 10); 5.12 (s, 4); 4.20 (d, 2); 4.12 (m, 1); 3.90 (d, 1); 3.18 (m, 1); 2.82 (m, 5); 2.05 (m, 2); 0.90 (m, 9); (d, 3). MS: m/e 749 (M$^+$+1). Analysis for C$_{44}$H$_{52}$N$_4$O$_7$: Calc.: C, 70.57; H, 7.00; N, 7.48; Found: C, 70.31; H, 7.11; N, 7.76.

Example 2

1,6-Diphenyl-2(S),5(S)-di[N-[2(S)-N(benzyloxycarbonyl)aminobutanoyl]amino]-3,4-cis-epoxyhexane The titled compound was prepared substantially in accordance with the procedure detailed in Example 1 using 194 mg (0.818 mmol) of 2(S)-N(benzyloxycarbonyl)aminobutanoic acid, 12 mg (0.082 mmol) of HOBT.H$_2$O, 104 μL (0.818 mmol) of NMM and 370 mg (0.818 mmol) of BOP, 80 μL (0.40 mmol) of N,N-dicyclohexylamine and 71 mg (0.20 mmol) of the subtitled intermediate of Preparation 1G to provide 21 mg of the desired compound.

NMR (80% CDCl$_3$/20% CD$_3$OD): δ 7.35 (s, 10); 7.20 (m, 10); 5.15 (s, 4); 4.25 (d, 2); 4.10 (m, 1); 3.90 (d, 1); 3.15 (m, 1); 2.80 (m, 5); 1.45 (m, 4); 0.8 (m, 6).

Example 3

1,6-Diphenyl-2(S),5(S)-di[N-[2(S)-N(quinolin-2-ylcarbonyl)amino-3-cyanopropanoyl]amino]-3,4-cis-epoxyhexane The titled compound was prepared substantially in accordance with the procedure detailed in Example 1 using 163 mg (0.605 mmol) of 2(S)-N(quinolin-2-ylcarbonyl)amino-3-cyanopropanoic acid, 8.1 mg (0.06 mmol) of HOBT.H$_2$O, 67 μL (0.60 mmol) of NMM and 268 mg (0.605 mmol) of BOP, 61 μL (0.30 mmol) of N, N-dicyclohexylamine and 53 mg(0.15 mmol) of the subtitled intermediate of Preparation 1G to provide 32 mg of a mixture of diastereomers. These diastereomers were separated using reverse phase high performance liquid chromatography (HPLC) (1:1:1 acetonitrile/methanol/water containing 0.36% acetic acid) to provide 7 mg of the desired compound.

NMR (80% CDCl$_3$/20% CD$_3$OD): δ8.20 (m, 6); 7.75 (m, 6); 7.0 (m, 10); 4.75 (m, 2); 4.25 (m, 2); 3.0 (m, 8).

MS: m/e 785 (M$^+$+1).

Example 4

1,6-Diphenyl-2(S),5(S)-di[N-[2(S)-N[(quinolin-2-ylmethoxy)carbonyl]amino-3-methylbutanoyl]amino]-3,4-cis-epoxyhexane The titled compound was prepared substantially in accordance with the procedure detailed in Example 1 using 231 mg (0.762 mmol) of 2(S)-N-[(quinolin-2-ylmethoxy)carbonyl]amino-3-methylbutanoic acid, 11 mg (0.076 mmol) of HOBT.H$_2$O, 92 μL (0.84 mmol) of NMM and 337 mg (0.762 mmol) of BOP, 76 μL (0.38 mmol) of N,N-dicyclohexylamine and 66 mg (0.19 mmol) of the subtitled intermediate of Preparation 1G to provide 70 mg of crude product. This mixture was purified using reverse phase HPLC (35% acetonitrile/35% methanol/30% water containing 0.5% acetic acid) to provide 7 mg of a material which was 92% of the desired titled product.

NMR (80% CDCl$_3$/20% CD$_3$OD): δ8.05 (m, 2); 7.72 (m, 2); 7.45 (m, 2); 7.10 (m, 10); 5.35 (s, 4); 4.15 (m, 2); 3.95 (m, 2); 3.10 (d, 1); 2.80 (m, 5); 2.0 (m, 2); 0.8 (m, 12).

Example 5

1,6-Diphenyl-2(S),5(S)-di[N-[2(S)-N(benzyloxycarbonyl)amino-3-carbamoylpropanoyl]amino]-3,4-cis-epoxyhexane The titled compound was prepared substantially in accordance with the procedure detailed in Example 1 using 218 mg (0.818 mmol) of 2(S)-N(benzyloxycarbonyl)amino-3-carbamoylpropanoic acid, 12 mg (0.082 mmol) of HOBT.H$_2$O, 104 μL (0.818 mmol) of NMM and 362 mg (0.818 mmol) of BOP, 80 μL (0.40 mmol) of N,N-dicyclohexylamine and 71 mg (0.20 mmol) of the subtitled intermediate of Preparation 1G to provide 7 mg of a material that was 80–85% desired titled product.

Example 6

1,6-Diphenyl-2(S),5(S)-di[N-[2(S)-N(benzyloxycarbonyl)amino-3-cyanopropanoyl]amino]-3,4-cis-epoxyhexane The titled compound was prepared substantially in accordance with the procedure detailed in Example 1 using 137 mg (0.552 mmol) of 2(S)-N(benzyloxycarbonyl)amino-3cyanopropanoic acid, 8 mg (0.06 mmol) of HOBT.H$_2$O, 61 μL (0.552 mmol) of NMM and 244 mg (0.552 mmol) of BOP, 55 μL (0.28 mmol) of N,N-dicyclohexylamine and 49 mg (0.14 mmol) of the subtitled intermediate of Preparation 1G. The resultant material was purified using reverse phase HPLC (32.5% acetonitrile/32.5% methanol/35% water containing 0.2% ammonium acetate) to provide 38 mg of the desired titled product.

NMR (90% CDCl$_3$/10% D$_2$O): δ7.10 (m, 20); 5.10 (s, 4); 4.58 (m, 1); 4.40 (m, 1); 4.25 (m, 1); 4.10 (m, 2); 3.22 (m, 1); 2.80 (m, 8).

MS: m/e 743 (M$^+$+1).

Analysis for $C_{42}H_{42}N_6O_7$: Calc.: C, 67.91; H, 5.70; N, 11.31; Found: C, 68.02; H, 5.84; N, 11.06.

Example 7

1,6-Diphenyl-2(S),5(S)-di[N-[2(S)-N(benzyloxycarbonyl)amino-3-pyrazol-1-ylpropanoyl]amino]3,4-cis-epoxyhexane The titled compound was prepared substantially in accordance with the procedure detailed in Example 1 using 250 mg (0.901 mmol) of 2(S)-N(benzyloxycarbonyl)amino-3-pyrazol-1-ylpropanoic acid, 12 mg (0.09 mmol) of HOBT.H₂O, 100 μL (0.901 mmol) of NMM and 398 mg (0.901 mmol) of BOP, 90 μL (0.45 mmol) of N,N-dicyclohexylamine and 80 mg (0.22 mmol) of the subtitled intermediate of Preparation 1G. The resultant material was purified using reverse phase HPLC (37.5% acetonitrile/37.5% methanol/25% water containing 0.5% ammonium acetate) to provide the desired titled product.

Example 8

1,6-Diphenyl-2(S),5(S)-di[N-[2(S)-N(pyrid-2-ylmethoxycarbonyl)amino-3-methylbutanoyl]amino]-3,4-cis-epoxyhexane The titled compound was prepared substantially in accordance with the procedure detailed in Example 1 using 328 mg (1.31 mmol) of 2(S)-N(pyrid-2-ylmethoxycarbonyl)amino- 3-methylbutanoic acid, 17.6 mg (0.13 mmol ) of HOBT.H₂O, 143 μL (1.30 mmol) of NMM and 575 mg (1.30 mmol) of BOP, 124 μL (0.619 mmol) of N,N-dicyclohexylamine and 110 mg (0.310 mmol) of the subtitled intermediate of Preparation 1G to provide 195 mg of crude material. This material was purified using reverse phase HPLC (30% acetonitrile/25% methanol/45% water containing 0.05% ammonium acetate) to provide 95 mg of the desired product.

NMR (80% d₆-DMSO/20% D₂O): δ8.42 (s, 1); 7.72 (m, 1); 7.25 (m, 2); 7.05 (m, 10); 5.02 (m, 4); 4.0 (m, 2); 3.75 (m, 2); 3.15 (d, 1); 2.70 (m, 5); 1.85 (m, 2); 0.7 (m, 12).

MS: m/e 751 (M⁺+1).

Analysis for $C_{42}H_{50}N_6O_7$: Calc.: C, 67.18; H, 6.71; N, 11.19; Found: C, 67.39; H, 6.87; N, 11.92.

Example 9

1,6-Diphenyl-2(S),5(S)-di[N-[2(S)-N(benzyloxycarbonyl)amino-3-imidazol-4-yl-propanoyl]amino]-3,4-cis-epoxyhexane The titled compound was prepared substantially in accordance with the procedure detailed in Example 1 using 248 mg (0.856 mmol) of 2-N(benzyloxycarbonyl)amino-3-imidazol-4-ylpropanoic acid, 12 mg (0.085 mmol) of HOBT.H₂O, 94 μL (0.86 mmol) of NMM and 378 mg (0.856 mmol) of BOP, 87 μL (0.438 mmol) of N,N-dicyclohexylamine and 76 mg (0.214 mmol) of the subtitled intermediate of Preparation 1G. The resultant material was purified using reverse phase HPLC (35% acetonitrile/35% methanol/30% water containing 0.3% ammonium acetate) to provide 19 mg of the desired product.

NMR (80% d₆-DMSO/20% D₂O): δ7.50 (s, 2); 7.10 (m, 20); 6.68 (s, 2); 4.95 (s, 4); 4.05 (m, 4); 3.20 (m, 1); 2.60 (m, 8).

Example 10

1,6-Diphenyl-2(S),5(S)-di[N-[2(S)-N[(quinolin-2-ylmethoxy)carbonyl]aminobutanoyl]amino]-3,4-cis-epoxyhexane The titled compound was prepared substantially in accordance with the procedure detailed in Example 1 using 333 mg (1.154 mmol) of 2(S)-N[(quinolin-2-ylmethoxy)carbonyl]aminobutanoic acid, 16 mg (0.12 mmol) of HOBT.H₂O, 128 μL (1.16 mmol) of NMM and 510 mg (1.15 mmol) of BOP, 112 μL (0.563 mmol) of N,N-dicyclohexylamine and 100 mg (0.282 mmol) of the subtitled intermediate of Preparation 1G. The resultant material was purified using reverse phase HPLC (45% acetonitrile/35% methanol/20% water containing 0.5% ammonium acetate) to provide 75 mg of the desired titled product.

NMR (CD₃OD): δ8.25 (m, 2); 7.90 (m, 2); 7.80 (m, 2); 7.70 (m, 2); 7.50 (m, 4); 7.10 (m, 10); 5.3 (m, 4); 4.2 (m, 3); 4.0 (m, 2); 3.22 (m, 1); 2.80 (m, 4); 1.65 (m, 2); 1.55 (m, 2); 0.85 (m, 6).

MS: m/e 823 (M⁺+1).

Analysis for $C_{48}H_{50}N_6O_7$: Calc.: C, 70.05; H, 6.12; N, 10.21; Found: C, 69.85; H, 6.14; N, 10.37.

Example 11

1,6-Diphenyl-2(S),5(S)-di[N-[2(S)-N(benzyloxycarbonyl)amino-3-methylthiopropanoyl]amino]-3,4-cis-epoxyhexane The titled compound was prepared substantially in accordance with the procedure detailed in Example 1 using 318 mg (1.18 mmol) of 2(S)-N(benzyloxycarbonyl)amino-3-methylthiopropanoic acid, 16 mg (0.12 mmol) of HOBT.H₂O, 132 μL (1.2 mmol) of NMM and 523 mg (1.18 mmol) of BOP, 0.112 mL (0.563 mmol) of N,N-dicyclohexylamine and 100 mg (0.282 mmol) of the subtitled intermediate of Preparation 1G. The resultant material was purified using reverse phase HPLC (40% acetonitrile/35% methanol/25% water containing 0.2% ammonium acetate) to provide 27 mg of the desired titled product.

NMR (CD₃OD): δ7.30 (m, 10); 7.15 (m, 10); 5.08 (s, 4); 4.45 (m, 1); 4.25 (m, 2); 4.15 (m, 1); 4.0 (m, 1); 3.25 (m, 1); 2.70 (m, 8); 2.02 (s, 6).

MS: m/e 784 (M⁺).

Example 12

1,6-Diphenyl-2(S),5(S)-di[N-[2(S)-N(benzyloxycarbonyl)amino-4-carbamoylbutanoyl]amino]-3,4-cis-epoxyhexane The titled compound was prepared substantially in accordance with the procedure detailed in Example 1 using 331 mg (1.18 mmol) of 2(S)-N(benzyloxycarbonyl)amino-4-carbamoylbutanoic acid, 16 mg (0.12 mmol) of HOBT.H₂O, 132 μL (1.2 mmol) of NMM and 523 mg(1.18 mmol) of BOP, 0.112 mL (0.563 mmol) of N,N-dicyclohexylamine and 100 mg (0.282 mmol) of the subtitled intermediate of Preparation 1G. The resultant material was purified using reverse phase HPLC (32.5% acetonitrile/32.5% methanol/35% water containing 0.5% ammonium acetate) to provide 28 mg of the desired titled product.

NMR (CD₃OD): δ7.2 (m, 20); 5.10 (s, 4); 4.30 (m, 1); 4.10 (m, 3); 3.18 (d, 1); 2.80 (m, 5); 2.2 (m, 4); 1.90 (m, 4).

MS: m/e 807 (M⁺+1).

Analysis for $C_{44}H_{50}N_6O_9$: Calc.: C, 65.49; H, 6.25; N, 10.41; Found: C, 65.25; H, 6.30; N, 10.21.

Example 13

1,6-Diphenyl-2(S),5(S)-di[N-[2(S)-N(pyrid-2-ylmethoxycarbonyl)amino-4-methylpentanoyl]amino]-3,4-cis-epoxyhexane The titled compound was prepared substantially in accordance with the procedure detailed in Example 1 using 315 mg (1.18 mmol) of 2(S)-N(pyrid-2-ylmethoxycarbonyl)amino-4-methylpentanoic acid, 16 mg (0.12 mmol) of HOBT.H₂O, 0.132 mL (1.2 mmol) of NMM and 523 mg (1.18 mmol) of BOP, 0.112 mL (0.563 mmol) of N,N- dicyclohexylamine and 100 mg (0.282 mmol) of the subtitled intermediate of Preparation 1G. The resultant material was purified using reverse phase HPLC (32.5% acetonitrile/ 32.5% methanol/35% water containing 0.5% ammonium acetate) to provide 76 mg of the desired titled product.

NMR (CD$_3$OD): δ8.4 (S, 2); 7.75 (m, 2); 7.40 (m, 4); 7.25 (m, 4); 7.10 (m, 10); 5.10 (s, 4); 4.10 (m, 4); 4.00 (d, 1); 3.25 (d, 1); 2.80 (m, 4); 1.4 (m, 4); 0.8 (m, 12).

MS: m/e 778 (M$^+$).

Analysis for C$_{44}$H$_{54}$N$_6$O$_7$: Calc.: C, 67.85; H, 6.99; N, 10.79; Found: C, 67.60; H, 6.93; N, 10.76.

Example 14

1,6-Diphenyl-2(S),5(S)-di[N-[2(S)-N(benzyloxycarbonyl)amino-3(S)-methylpropanoyl]amino]-3,4-cis-epoxyhexane The titled compound was prepared substantially in accordance with the procedure detailed in Example 1 using 306 mg (1.15 mmol) of 2(S)-N(benzyloxycarbonyl)amino-3(S)methylpentanoic acid, 16 mg (0.12 mmol) of HOBT.H$_2$O, 128 μL (1.16 mmol) of NMM and 510 mg (1.154 mmol) of BOP, 112 μL (0.563 mmol) of N,N-dicyclohexylamine and 100 mg (0.282 mmol) of the subtitled intermediate of Preparation 1G to provide a tan solid. This solid was purified using reverse phase HPLC (45% acetonitrile/35% methanol/20% water containing 0.5% ammonium acetate) to provide 46 mg of the desired titled product.

NMR (CD$_3$OD): δ7.35 (m, 10); 7.15 (s, 10); 5.10 (s, 4); 4.2 (m, 3); 4.0 (q, 1); 3.92 (d, 1); 3.22 (m, 1); 2.80 (m, 4); 1.75 (m, 2); 1.45 (m, 2); 1.1 (m, 2); 0.8 (m, 12).

MS: m/e 777 (M$^+$+1).

Analysis for C$_{46}$H$_{56}$N$_4$O$_6$: Calc.: C, 71.11; H, 7.26; N, 7.21; Found: C, 70.84; H, 7.36; N, 7.29.

Example 15

1,6-Diphenyl-2(S),5(S)-di[N-[2(S)-N[(quinolin-2-ylmethoxy)carbonyl]amino-3(S)-methylpentanoyl]amino]-3,4-cis-epoxyhexane The titled compound was prepared substantially in accordance with the procedure detailed in Example 1 using 365 mg (1.15 mmol) of 2(S)-N[(quinolin-2-ylmethoxy)carbonyl]amino-3(S)-methylpentanoic acid, 16 mg (0.12 mmol) of HOBT.H$_2$O, 0.128 mL (1.16 mmol) of NMM and 510 mg (1.154 mmol) of BOP, 112 μL (0.563 mmol) of N,N-dicyclohexylamine and 100 mg (0.282 mmol) of the subtitled intermediate of Preparation 1G. The resultant material was purified using reverse phase HPLC (45% acetonitrile/ 30% methanol/20% water containing 0.5% ammonium acetate) to provide 90 mg of the desired titled product.

NMR (CD$_3$OD): δ8.25 (d, 2); 7.95 (d, 2); 7.85 (d, 2); 7.70 (m, 2); 7.55 (m, 4); 7.10 (m, 10); 5.35 (m, 4); 4.25 (m, 2); 4.20 (d, 1); 4.0 (m, 2); 3.22 (m, 1); 2.80 (m, 4); 1.8 (m, 2); 1.5 (m, 1); 1.3 (m, 1); 1.1 (m, 2); 0.8 (m, 12).

MS: m/e 879 (M$^+$+1).

Analysis for C$_{52}$H$_{58}$N$_6$O$_7$: Calc.: C, 71.05; H, 6.65; N, 9.56; Found: C, 71.05; H, 6.70; N, 9.75.

Example 16

1,6-Diphenyl-2(S),5(S)-di[N-[2(S)-N-[[N(methyl)-N(pyrid-2-ylethyl)amino]carbonyl]amino-3-methylbutanoyl]amino] -3,4-cis-epoxyhexane The titled compound was prepared substantially in accordance with the procedure detailed in Example 1 using 522 mg (1.87 mmol) of 2(S)-N-[[N(methyl)-N(pyrid-2-ylethyl)amino]carbonyl]amino-3-methylbutanoic acid, 16 mg (0.115 mmol) of HOBT.H$_2$O, 0.207 mL (1.88 mmol) of NMM and 825 mg (1.87 mmol) of BOP, 183 μL (0.919 mmol) of N,N-dicyclohexylamine and 162 mg (0.455 mmol) of the subtitled intermediate of Preparation 1G. The resultant material was purified using reverse phase HPLC (45% acetonitrile/20% methanol/35% water containing 0.4% ammonium acetate) to provide 42 mg of the desired product.

NMR (CD$_3$OD): δ8.42 (m, 2); 7.70 (m, 2); 7.20 (m, 14); 4.22 (m, 3); 4.0 (q, 1); 3.85 (d, 1); 3.6 (m, 4); 3.22 (m, 1); 2.95 (m, 4); 2.82 (s, 6); 2.80 (m, 4); 1.95 (m, 2); 0.8 (m, 12).

Example 17

1,6-Diphenyl-2(S),5(S)-di[N-[2(S)-N[(8-fluoroquinolin-2-ylmethoxy)carbonyl]amino-3-methylbutanoyl]amino]-3,4-cis-epoxyhexane The titled compound was prepared substantially in accordance with the procedure detailed in Example 1 using 286 mg (0.892 mmol) of 2(S)-N[(8-fluoroquinolin-2-ylmethoxy)carbonyl]amino-3-methylbutanoic acid, 12 mg (0.089 mmol) of HOBT.H$_2$O, 0.100 mL (1.89 mmol) of NMM and 395 mg (0.892 mmol) of BOP, 87 μL (0.44 mmol) of N,N-dicyclohexylamine and 78 mg (0.22 mmol) of the subtitled intermediate of Preparation 1G. The resultant material was purified using reverse phase HPLC (35% acetonitrile/35% methanol/30% water containing 0.5% ammonium acetate) to provide 34 mg of the desired product.

NMR (CD$_3$OD): δ8.25 (d, 2); 7.60 (m, 4); 7.45 (m, 4); 7.10 (m, 10); 5.35 (m, 4); 4.25 (m, 2); 4.15 (d, 1); 4.05 (m, 1); 3.95 (m, 1); 3.25 (m, 1); 2.80 (m, 4); 2.0 (m, 2); 0.85 (m, 12).

MS: m/e 888 (M$^+$+2).

Example 18

1,6-Diphenyl-2(S),5(S)-di[N-[2(S)-N-[[N(methyl)-N(quinolin-2-ylmethyl)amino]carbonyl]aminobutanoyl] amino]-3,4-cis-epoxyhexane The titled compound was prepared substantially in accordance with the procedure detailed in Example 1 using 187 mg (0.62 mmol) of 2(S)-N-[[N(methyl)-N(quinolin-2-ylmethyl)amino]carbamoyl]aminobutanoic acid, 9 mg (0.06 mmol) of HOBT.H$_2$O, 70 μL (0.620 mmol) of NMM and 274 mg (0.620 mmol) of BOP, 71 μL (0.355 mmol) of N,N-dicyclohexylamine and 63 mg (0.18 mmol) of the subtitled intermediate of Preparation 1G. The resultant material was purified using reverse phase HPLC (50% acetonitrile/20% methanol/30% water containing 0.5% ammonium acetate) to provide 50 mg of the desired product.

NMR (CD$_3$OD): d 8.25 (dd, 2); 7.95 (m, 2); 7.85 (m, 2); 7.70 (m, 2); 7.55 t, 2); 7.40 (dd, 2); 7.15 (m, 10); 4.80 (ABX, 4); 4.35 (m, 2); 4.15 (m, 2); 4.0 m, 1); 3.25 (m, 1); 3.02 (s, 3); 2.97 s, 3); 2.80 (m, 4); 1.7 (m, 4); 0.85 (m, 6).

MS: m/e 849 (M$^+$+1).

Example 19

1,6-Diphenyl-2(S),5(S)-di[N-[2(S)-N[[N(methyl)-N(quinolin-2-ylmethyl)amino]carbonyl]amino-3(S)methylpentanoyl]amino]-3,4-cis-epoxyhexane The titled compound was prepared substantially in accordance with the procedure detailed in Example 1 using 232 mg (0.704 mmol) of 2(S)-N-[[N(methyl)-N(quinolin-2-ylmethyl) amino]carbonyl]amino-3(S)-methylpentanoic acid, 10 mg (0.070 mmol) of HOBT.H$_2$O, 78 μL (0.70 mmol) of NMM and 312 mg (0.704 mmol) of BOP, 80 μL (0.40 mmol) of N,N-dicyclohexylamine and 72 mg (0.201 mmol) of the subtitled intermediate of Preparation 1G. The resultant material was purified using reverse phase HPLC (50% acetonitrile/20% methanol/30% water containing 0.5% ammonium acetate) to provide the desired titled product.

NMR (CD$_3$OD): δ8.25 (dd, 2); 7.95 (m, 2); 7.85 (d, 2); 7.70 (m, 2); 7.55 t, 2); 7.40 (d, 2); 7.15 (m, 10); 4.75 (ABX, 4); 4.38 (d, 1); 4.28 (t, 1); 4.20 m, 1); 4.0 (m, 2); 3.25 (m, 1); 3.02 s, 6); 2.75 (m, 4); 1.78 (m, 2); 1.05–1.45 (m, 4); 0.75 (m, 12).

MS: m/e 906 (M$^+$+2).

Example 20

1,6-Diphenyl-2(S),5(S)-di[N-[2(S)-N(benzyloxycarbonyl)amino]propanoyl]amino-3,4-cis-epoxyhexane The titled compound was prepared substantially in accordance with the procedure detailed in Example 1 using 94 mg (0.42 mmol) of 2(S)-N(benzyloxycarbonyl)aminopropanoic acid, 6 mg (0.04 mmol) of HOBT.H$_2$O, 46 μL (0.42 mmol) of NMM and 187 mg (0.42 mmol) of BOP, 56 μL (0.28 mmol) of N,N-dicyclohexylamine and 50 mg (0.14 mmol) of the subtitled intermediate of Preparation 1G. The resultant material was purified using reverse phase HPLC (50% acetonitrile/20% methanol/30% water containing 0.5% ammonium acetate) to provide 15 mg of the desired titled product.

NMR (CD$_3$OD): δ7.30 (m, 10); 7.10 (m, 10); 5.05 (s, 4); 4.30 (m, 1); 4.20 (m, 1); 4.1 (m, 2); 3.95 (m, 1); 3.20 (m, 1); 2.75 (m, 4); 1.22 (m, 6).

MS: m/e 694 (M$^+$+2).

Example 21

1,6-Diphenyl-2(S),5(S)-di[N-[2(S)-N[[N(methyl)-N(quinolin-2-ylmethyl)amino]carbonyl]aminopentanoyl]amino]-3,4-cis epoxyhexane The titled compound was prepared substantially in accordance with the procedure detailed in Example 1 using 90 mg (0.28 mmol) of 2(S)-N-[[N(methyl)-N(quinolin-2-ylmethyl)amino]carbonyl]aminopentanoic acid, 4 mg (0.03 mmol) of HOBT.H$_2$O, 32 μL (0.28 mmol) of NMM and 126 mg (0.285 mmol) of BOP, 41 μL (0.20 mmol) of N,N-dicyclohexylamine and 36.2 mg (0.102 mmol) of the subtitled intermediate of Preparation 1G. The resultant material was purified using reverse phase HPLC (50% acetonitrile/20% methanol/30% water containing 0.5% ammonium acetate) to provide 32 mg of the desired titled product.

NMR (CD$_3$OD): δ8.25 (dd, 2); 7.95 (m, 2); 7.85 (m, 2); 7.70 (m, 2); 7.52 (t, 2); 7.40 (dd, 2); 7.15 (m, 10); 4.75 (ABX, 4); 4.42 (m, 1); 4.30 (m, 1); 4.18 (m, 2); 3.97 (m, 1); 3.25 (m, 1); 3.03 (s, 3); 2.98 (s, 3); 2.78 (m, 4); 1.65 (m, 4); 1.25 (m, 4); 0.85 (m, 6).

MS: m/e 878 (M$^+$+2).

Example 22

1,6-Diphenyl-2(S),5(S)-di[N-[2(S)-N[[N(methyl)-N(quinolin-2-ylmethyl)amino]carbonyl]aminohexanoyl]amino]-3,4-cis-epoxyhexane The titled compound was prepared substantially in accordance with the procedure detailed in Example 1 using 130 mg (0.394 mmol) of 2(S)-N-[[N(methyl)-N(quinolin-2-ylmethyl)amino]carbonyl]aminohexanoic acid, 5.3 mg (0.039 mmol) of HOBT.H$_2$O, 45 μL (0.39 mmol) of NMM and 175 mg (0.394 mmol) of BOP, 45 μL (0.20 mmol) of N,N-dicyclohexylamine and 40 mg (0.11 mmol) of the subtitled intermediate of Preparation 1G. The resultant material was purified using reverse phase HPLC (50% acetonitrile/20% methanol/30% water containing 0.5% ammonium acetate) to provide 45 mg of the desired titled product.

$^1$H NMR (CD$_3$OD): δ8.25 (dd, 2); 7.95 (m, 2); 7.85 (dd, 2); 7.70 (m, 2); 7.55 (t, 2); 7.40 (dd, 2); 7.15 (m, 10); 4.75 (ABX, 4); 4.40 (m, 1); 4.25 (m, 1); 4.15 (m, 2); 3.95 (m, 1); 3.25 (m, 1); 3.05 (s, 3); 3.0 (s, 3); 2.80 (m, 4); 1.60 (m, 4); 1.20 (m, 8); 0.82 (m, 6).

MS: m/e 906 (M$^+$+2).

Example 23

1,6-Diphenyl-2(S),5(S)-di[N-[2(S)-N(pyrid-3-ylmethoxycarbonyl)amino-3,3-dimethylbutanoyl]amino]-3,4-cis-epoxyhexane The titled compound was prepared substantially in accordance with the procedure detailed in Example 1 using 214.9 mg (0.807 mmol) of 2(S)-N(pyrid-3-ylmethoxycarbonyl)amino-3,3-dimethylbutanoic acid, 11.2 mg (0.0829 mmol) of HOBT.H$_2$O, 100 μL (0.909 mmol) of NMM and 344.0 mg (0.778 mmol) of BOP, 80 μL (0.40 mmol) of N,N-dicyclohexylamine and 69.1 mg (0.194 mmol) of the subtitled intermediate of Preparation 1G. The resultant material was purified using reverse phase HPLC (50% acetonitrile/20% methanol/30% water containing 0.5% ammonium acetate) to provide 43.6 mg of a white solid which was a mixture of 4 diastereomers.

NMR (CD$_3$OD): δ8.57 (br.s, 2); 8.47 (m, 2); 7.84 (d, 2); 7.42 (m, 2); 6.96–7.27 (m, 10); 5.15 (AB, 4); 4.14–4.24 (m, 2); 3.89 (br.s, 1); 3.25 (m, 1); 3.07 (m, 2); 2.61–2.97 (m, 4); 0.90 (m, 18).

MS: m/e 780 (M$^+$+2).

Example 24

1,6-Diphenyl-2(S),5(S)-di[N-[2(S)-N[[N(methyl)-N(pyrid-2-ylmethyl)amino]carbonyl]amino-3(S)-methylpentanoyl]amino]-3,4-cis-epoxyhexane The titled compound was prepared substantially in accordance with the procedure detailed in Example 1 using 142.0 mg (0.508 mmol) of 2(S)-N-[[N(methyl)-N(pyrid-2-ylmethyl)amino]carbonyl]amino-3(S)-methylpentanoic acid, 7.5 mg .(0.056 mmol) of HOBT.H$_2$O, 60 μL (0.55 mmol) of NMM and 243.8 mg (0.551 mmol) of BOP, 63 μL (0.32 mmol) of N,N-dicyclohexylamine and 52.5 mg (0.148 mmol) of the subtitled intermediate of Preparation 1G. The resultant material was purified using reverse phase HPLC (40% acetonitrile/20% methanol/40% water containing 0.5% ammonium acetate) to provide 10.9 mg of the desired titled product.

NMR (CD$_3$OD): δ8.47 (br.s, 2); 7.76 (m, 2); 7.03–7.33 (m, 14); 4.46–4.64 (m, 4); 4.13–4.39 (m, 3); 4.04 (q, 2); 3.25 (s, 1); 2.98 (s, 6); 2.67–2.98 (m, 4); 1.88 (m, 2); 1.43 (m, 2); 1.10 (m, 2); 0.84 (m, 12).

MS: m/e 807 (M$^+$+3).

Example 25

1,6-Diphenyl-2(S),5(S)-di[N-[2(S)-N(pyrid-2-ylmethoxycarbonyl)amino]hexanoyl]amino-3,4-cis-epoxyhexane The titled compound was prepared substantially in accordance with the procedure detailed in Example 1 using 136.7 mg (0.513 mmol) of 2(S)-N(pyrid-2-ylmethoxycarbonyl)aminohexanoic acid, 10.4 mg (0.0770 mmol) of HOBT.H$_2$O, 0.060 mL (0.55 mmol) of NMM and 242.8 mg (0.549 mmol) of BOP, 62 μL (0.311 mmol) of N,N-dicyclohexylamine and 51.4 mg (0.145 mmol) of the subtitled intermediate of Preparation 1G. The resultant material was purified using reverse phase HPLC (50% acetonitrile/20% methanol/30% water containing 0.5% ammonium acetate) to provide 24.5 mg of the desired titled product.

NMR (CD$_3$OD): δ8.47 (m, 2); 7.81 (m, 2); 7.02–7.53 (m, 14); 5.18 (AB, 4); 4.22 (m, 3); 4.00 (m, 2); 3.25 (m, 1); 2.70–2.94 (m, 4); 1.05–1.73 (m, 12); 0.90 (m, 6).
MS: m/e 780 (M$^+$+2).

Example 26

1,6-Diphenyl-2(S),5(S)-di[N-[2(S)-N(quinolin-2-ylcarbonyl)amino-3-methylbutanoyl]amino]-3,4-cis-epoxyhexane The titled compound was prepared substantially in accordance with the procedure detailed in Example 1 using 223 mg (0.818 mmol) of 2(S)-N(quinolin-2-ylcarbonyl)amino-3-methylbutanoic acid, 11.1 mg (0.0818 mmol) of HOBT.H$_2$O, 0.090 mL (0.82 mmol) of NMM and 362 mg (0.818 mmol) of BOP, 73 μL (0.31 mmol) of diisopropylethylamine and 125 mg (0.200 mmol) of the di-p-toluenesulfonate salt of the subtitled intermediate of Preparation 1G. The resultant material was purified using reverse phase HPLC (45% acetonitrile/35% methanol/20% water containing 0.5% ammonium acetate) to provide 10 mg of material that comprised 84% of the desired titled product.
NMR (CD$_3$OD): δ8.15 (m, 2); 7.70 (m, 6); 7.0 (m, 10); 4.45 (m, 1); 4.25 (m, 2); 4.05 (m, 1); 3.2 (dd, 1); 2.8 (m, 5); 2.15 (m, 1); 2.05 (m, 1); 0.9 (m, 12).
MS: m/e 791 (M$^+$+1).

Example 27

1,6-Diphenyl-2(S),5(S)-di [N-[2(S)-N[[N(methyl)-N(quinolin-2-ylmethyl)amino]carbonyl]amino-3-cyanopropanoyl]amino]-3,4 -cis-epoxyhexane The titled compound was prepared substantially in accordance with the procedure detailed in Example 1 using 165 mg (0.528 mmol) of 2(S)-N-[[N(methyl)-N(quinolin-2-ylmethyl)amino]carbonyl]amino-3-cyanobutanoic acid, 10 mg (0.053 mmol) of HOBT.H$_2$O, 0.060 mL (0.53 mmol) of NMM and 234 mg (0.528 mmol) of BOP, 73 μL (0.37 mmol) of N,N-dicyclohexylamine and 65 mg (0.18 mmol) of the subtitled intermediate of Preparation 1G. The resultant material was purified using reverse phase HPLC (50% acetonitrile/20% methanol/30% water containing 0.5% ammonium acetate) to provide 49 mg of the desired titled product.
NMR (CD$_3$OD): δ8.28 (d, 2); 8.0 (d, 2); 7.88 (t, 2); 7.72 (t, 2); 7.57 (m, 2); 7.43 (t, 2); 7.18 (m, 10); 4.70 (m, 5); 4.20 (m, 3); 3.10 (d, 2); 3.00 (s, 3); 2.97 (s, 3); 2.85 (m, 8).
MS: m/e 872 (M$^+$+2).

Example 28

1,6-Diphenyl-2(S),5(S)-di[N-[2(S)-N[[N(methyl)-N(pyrid-2-ylmethyl)amino]carbonyl]aminobutanoyl]amino]-3,4-cis-epoxyhexane The titled compound was prepared substantially in accordance with the procedure detailed in Example 1 using 145.8 mg (0.580 mmol) of 2(S)-N-[[N(methyl)-N(pyrid-2-ylmethyl)amino]carbonyl]aminobutanoic acid, 17.0 mg (0.126 mmol) of HOBT.H$_2$O, 73.0 μL (0.664 mmol) of NMM and 281.4 mg (0.636 mmol) of BOP, 0.060 ml, (0.30 mmol) of N,N-dicyclohexylamine and 99.7 mg (0.281 mmol) of the subtitled intermediate of Preparation 1G. The resultant material was purified using reverse phase HPLC (35% acetonitrile/20% methanol/45% water containing 0.5% ammonium acetate) to provide 6 mg of the desired titled product as a white solid.
NMR (CDCl$_3$): δ8.50 (d, 2); 7.67 (m, 2); 7.02–7.31 (m, 15); 6.78 (d, 1); 6.03 (m, 1); 5.98 (m, 1); 4.34–4.60 (m, 4); 4.24 (t, 1); 3.95–4.19 (m, 3); 3.74 (s, 1); 3.27 (s, 1); 2.72–3.05 (m, 10); 1.83 (m, 2); 1.67 (m, 2); 0.89 (t, 6).
MS: m/e 749 (M$^+$+1).

Example 29

1,6-Diphenyl-2(S),5(S)-di[N-[2(S)-N(6-methylpyrid-2-ylmethoxycarbonyl)amino-3-methylbutanoyl]amino]-3,4-cis-epoxyhexane The titled compound was prepared substantially in accordance with the procedure detailed in Example 1 using 126.2 mg (0.474 mmol) of 2(S)-N-(6-methylpyrid-2-ylmethoxycarbonyl)amino-3-methylbutanoic acid, 5.4 mg (0.040 mmol) of HOBT.H$_2$O, 0,060 mL (0.55 mmol) of NMM and 229.6 mg (0.519 mmol) of BOP, 95 μL (0.48 mmol) of N,N-dicyclohexylamine and 73.2 mg (0.206 mmol) of the subtitled intermediate of Preparation 1G. The resultant material was purified using reverse phase HPLC (35% acetonitrile/20% methanol/45% water containing 0.5% ammonium acetate) to provide 36 mg of the desired titled product as a white solid.
NMR (CDCl$_3$): δ7.66 (t, 2); 7.03–7.51 (m, 14); 5.12 (m, 4); 3.86–4.21 (m, 5); 3.26 (m, 1); 2.64–2.95 (m, 4); 2.50 (s, 6); 2.00 (m, 2); 0.82 (m, 12).
MS: m/e 780 (M$^+$+2).

Example 30

1,6-Diphenyl-2(S),5(S)-di[N-[2 (S)-N(quinolin-2-ylmethoxy)carbonyl]amino-3,3-dimethylbutanoyl]amino]-3,4-cis-epoxyhexane The titled compound was prepared substantially in accordance with the procedure detailed in Example 1 using 138.9 mg (0.439 mmol) of 2(S)-N(quinolin-2-ylmethoxy)carbonyl]amino-3,3-dimethylbutanoic acid, 4.8 mg (0.036 mmol) of HOBT.H$_2$O, 54.5 μL (0.496 mmol) of NMM and 212.0 mg (0.479 mmol) of BOP, 86 μL (0.43 mmol) of N,N-dicyclohexylamine and 71.1 mg (0.200 mmol) of the subtitled intermediate of Preparation 1G. The resultant material was purified using reverse phase HPLC (50% acetonitrile/20% methanol/30% water containing 0.5% ammonium acetate) to provide 50 mg of the desired titled product.
NMR (CD$_3$OD): δ8.28 (d, 2); 7.98 (d, 2; 7.89 (d, 2); 7.73 (t, 2); 7.55 (m, 4); 6.97–7.27 (m, 10); 5.32 (m, 4); 4.29 (m, 2); 4.18 (s, 1; 4.03 (m, 1); 3.91 (s, 1); 3.29 (m, 1); 2.66–2.97 (m, 4); 0.97 (s, 9); 0.94 (s, 9).
MS: m/e 879 (M$^+$+1).
Analysis for C$_{52}$H$_{58}$N$_6$O$_7$: Calc.: C, 71.04; H, 6.65; N, 9.56; Found: C, 70.84; H, 6.57; N, 9.39.

Example 31

1,6-Diphenyl-2(S),5(S)-di[N-[2(S)-N-[N(pyrid-2-ylmethyl)amino]carbonyl]amino-3(S)-methylpentanoyl]amino]3,4-cis-epoxyhexane The titled compound was prepared substantially in accordance with the procedure detailed in Example 1 using 112.3 mg (0.423 mmol) of 2(S)-N-[[N(pyrid-2-ylmethyl)amino]carbonyl]amino-3-methylpentanoic acid, 6.5 mg (0.048 mmol) of HOBT.H$_2$O, 0.060 mL (0.55 mmol) of NMM and 212.8 mg (0.481 mmol) of BOP, 85 μL (0.43 mmol) of N,N-dicyclohexylamine and 67.2 mg (0.189 mmol) of the subtitled intermediate of Preparation 1G. The resultant material was purified by recrystallization from diethylether to provide 69 mg of the desired titled product.
NMR (d$_6$-DMSO): δ8.43 (s, 2); 8.25 (d, 1); 8.03 (d, 1); 7.72 (t, 2); 6.94–7.31 (m, 14); 6.70 (m, 2); 6.30 (m, 1); 6.14 (d, 1); 4.32 (m, 3); 3.87–4.09 (m, 4); 2.61–3.05 (m, 6); 1.57 (m, 2); 1.21 (m, 2); 0.91 (m, 2); 0.58–0.79 (m, 12).
MS: m/e 777 (M$^+$+1).

Example 32

1,6-Dinaphth-2-yl-2(S),5(S)-di[N-[2(S)-N-[[N(methyl)-N(quinolin-2-ylmethyl)amino]carbonyl]aminobutanoyl]amino-3,4-cis-epoxyhexane The titled compound was prepared substantially in accordance with the procedure detailed in Example 1 using 129.7 mg (0.430 mmol) of 2(S)-N-[[N(methyl)-N(quinolin-2-ylmethyl) amino]carbonyl]aminobutanoic acid, 5.1 mg (0.038 mmol) of HOBT.H$_2$O, 51 μL (0.47 mmol) of NMM and 199.9 mg (0.452 mmol) of BOP, 52.0 μL (0.261 mmol) of N,N-dicyclohexylamine and 54.8 mg (0.120 mmol) of the subtitled intermediate of Preparation 2G. The resultant material was purified using reverse phase HPLC (50% acetonitrile/20% methanol/30% water containing 0.5% ammonium acetate) to provide 16 mg of the desired titled product.

NMR (CDCl$_3$): δ8.67 (m, 3); 6.70–7.81 (m, 25); 6.33 (m, 2); 4.03–4.70 (m, 8); 3.67 (m, 1); 3.29 (m, 1); 2.72–3.08 (m, 10); 1.43–1.87 (m, 4); 0.82 (m, 6).

MS: m/e 948 (M$^+$).

Analysis for C$_{58}$H$_{60}$N$_8$O$_5$: Calc.: C, 73.39; H, 6.37; N, 11.80; Found: C, 73.15; H, 6.43; N, 11.60.

Example 33

1,6-Dinaphth-2-yl-2(S),5(S)-di[N-[2(S)-N-[[N(methyl)-N(pyrid-2-ylmethyl)amino]carbonyl]amino-3(S)-methylpentanoyl]amino]-3,4-cis-epoxyhexane The titled compound was prepared substantially in accordance with the procedure detailed in Example 1 using 136.8 mg (0.490 mmol) of 2(S)-N-[[N(methyl)-N(pyrid-2-ylmethyl)amino]carbonyl]amino-3-methylpentanoic acid, 5.6 mg (0.041 mmol) of HOBT.H$_2$O, 55 μL (0.50 mmol) of NMM and 237.1 mg (0.536 mmol) of BOP, 55.0 μL (0.276 mmol) of N,N-dicyclohexylamine and 57.4 mg (0.126 mmol) of the subtitled intermediate of Preparation 2G. The resultant material was purified using reverse phase HPLC (50% acetonitrile/20% methanol/30% water containing 0.5% ammonium acetate) to provide 40 mg of the desired titled product as a white solid.

NMR (CDCl$_3$): δ8.46 (d, 2); 7.10–7.87 (m, 21); 6.62 (d, 1); 6.08 (m, 2); 4.28–4.63 (m, 7); 4.16 (s, 2); 3.34 (s, 1); 2.97 (m, 10); 1.86 (m, 2); 1.39 (m, 2); 1.10 (m, 2); 0.85 (m, 12).

MS: m/e 904 (M$^+$).

Analysis for C$_{54}$H$_{64}$N$_8$O$_5$: Calc.: C, 71.66; H, 7.13; N, 12.38; Found: C, 71.48; H, 7.12; N, 12.08.

Example 34

1,6-Dinaphth-2-yl-2(S),5(S)-di[N-[2(S)-N-[[N(methyl)-N(pyrid-2-ylmethyl)amino]carbonyl]aminobutanoyl]amino]-3,4-cis-epoxyhexane The titled compound was prepared substantially in accordance with the procedure detailed in Example 1 using 77.9 mg (0.3 10 mmol of 2(S)-N-[[N(methyl)-N(pyrid-2-ylmethyl) amino]carbonyl]aminobutanoic acid, 5.2 mg (0.038 mmol) of HOBT.H$_2$O, 40 μL (0.37 mmol) of NMM and 152.0 mg (0.344 mmol) of BOP, 55.0 μL (0.276 mmol) of N,N-dicyclohexylamine and 57.2 mg (0.126 mmol) of the subtitled intermediate of Preparation 2G. The resultant material was purified using reverse phase HPLC (35% acetonitrile/20% methanol/45% water containing 0.5% ammonium acetate) to provide 13 mg of the desired titled product as a white solid.

NMR (CDCl$_3$): δ8.49 (m, 2); 7.01–7.79 (m, 20); 6.85 (d, 1); 6.56 (d, 1); 5.96 (m, 2); 3.78–4.64 (m, 8); 3.58 (s, 1); 3.37 (s, 1); 2.71–3.12 (m, 10); 1.43–1.89 (m, 4); 0.84 (m, 6).

MS: m/e 850 (M$^+$+2).

Example 35

1,6-Dinaphth-2-ylthio-2(S),5(S)-di[N-[2(S)-N-[[N(methyl)-N (pyrid-2-ylmethyl)amino]carbonyl]aminobutanoyl]amino]-3,4-cis-epoxyhexane The titled compound was prepared substantially in accordance with the procedure detailed in Example 1 using 58.4 mg (0.232 mmol) of 2(S)-N-[[N(methyl)-N(pyrid-2-ylmethyl) amino]carbonyl]aminobutanoic acid, 4.5 mg (0.033 mmol) of HOBT.H$_2$O, 30 μL (0.27 mmol) of NMM and 111.2 mg (0.251 mmol) of BOP, 38.0 μL (0.191 mmol) of N,N-dicyclohexylamine and 49.1 mg (0.0866 mmol) of the subtitled intermediate of Preparation 3G. The resultant material was purified using reverse phase HPLC (35% acetonitrile/20% methanol/45% water containing 0.5% ammonium acetate) to provide 52.4 mg of the desired titled product as a white solid.

NMR (CDCl$_3$): δ8.48 (m, 2); 8.13 (s, 1); 7.96 (s, 1); 6.55–7.83 (m, 20); 6.28 (m, 1); 6.14 (m, 1); 4.36–4.69 (m, 4); 4.25 (m, 2); 3.75 (m, 1); 3.52 (m, 3); 3.18 (m, 2); 3.07 (dd, 1); 2.98 (m, 7); 1.87 (m, 2); 1.69 (m, 2); 0.93 (t, 6).

MS: m/e 912 (M$^+$+1).

Analysis for C$_{50}$H$_{56}$N$_8$O$_5$S$_2$: Calc.: C, 65.77; H, 6.18; N, 12.27; Found: C, 65.75; H, 6.17; N, 12.03.

Example 36

1,8-Diphenyl-3(S),6(S)-di[N-[2(S)-N-(pyrid-2-ylmethoxycarbonyl)amino]-3-methylbutanoyl]amino]-4,5-cis-epoxyoctane The titled compound was prepared substantially in accordance with the procedure detailed in Example 1 using 262 mg (1.04 mmol) of 2(S)-N-[(pyrid-2-ylmethoxycarbonyl)amino]-3-methylbutanoic acid, 14 mg (0.10 mmol) of HOBT.H$_2$O, 115 μL (1.04 mmol) of NMM and 462 mg 1.04 mmol) of BOP, 103 μL (0.522 mmol) of N,N-dicyclohexylamine and 100 mg (0.261 mmol) of the subtitled intermediate of Preparation 4. The resultant material was purified using reverse phase HPLC (55% acetonitrile/25% methanol/20% water containing 0.5% ammonium acetate) to provide 101 mg of the desired titled product.

NMR (CD$_3$OD): δ8.4 (s, 2); 7.7 (t, 4); 7.40 (m, 2); 7.10 (m, 10); 5.18 (m, 4); 3.90 (m, 4); 2.95 (m, 2); 2.60 (m, 4); 2.05 (m, 4); 1.75 (m, 2); 0.95 (m, 12).

MS: m/e 778 (M$^+$).

Analysis for C$_{44}$H$_{54}$N$_6$O$_7$: Calc.: C, 67.85; H, 6.99; N, 10.79; Found: C, 68.07; H, 7.05; N, 10.65.

Example 37

1,10-Diphenyl-4(S),7(S)-di[N-[2(S)-N-[[N(methyl)-N(pyrid-2-ylmethyl)amino]carbonyl]aminobutanoyl]amino]-5,6-cis-epoxydecane The titled compound was prepared substantially in accordance with the procedure detailed in Example 1 using 128 mg (0.508 mmol) of 2(S)-N-[[N(methyl)-N(pyrid-2-ylmethyl)amino]carbonyl]aminobutanoic acid, 7 mg (0.05 mmol) of HOBT.H$_2$O, 60 μL (0.53 mmol) of NMM and 225 mg (0.508 mmol) of BOP, 92 μL (0.46 mmol) of N,N-dicyclohexylamine and 95 mg (0.23 mmol) of the subtitled intermediate of Preparation 5. The resultant material was purified using reverse phase HPLC (50% acetonitrile/20% methanol/30% water containing 0.5% ammonium acetate) to provide 110 mg of the desired titled product.

NMR (CD$_3$OD): δ8.45 (br.s, 2); 7.75 (t, 2); 7.25 (m, 4); 7.13 (m, 10); 4.55 (AB, 4); 4.35 (m, 1); 4.15 (m, 2); 3.98 (m, 1); 3.85 (m, 1); 3.35 (m, 1); 2.95 (s, 6); 2.55 (m, 4); 1.80 (m, 4); 1.60 (m, 8); 0.96 (m, 6).

MS: m/e 806 (M$^+$+2).

Example 38

1,10-Diphenyl-4(S),7(S)-di[N-[2(S)-N-[[N(methyl)-N(quinolin-2-ylmethyl)amino]carbonyl]aminobutanoyl]amino]-5,6-cis-epoxydecane The titled compound was prepared substantially in accordance with the procedure detailed in Example 1 using 145 mg (0.480 mmol) of 2(S)-N-[[N(methyl)-N(quinolin-2-ylmethyl)amino]carbonyl]aminobutanoic acid, 6.5 mg (0.048 mmol) of HOBT.H$_2$O, 53 µL (0.48 mmol) of NMM and 212 mg (0.480 mmol) of BOP, 87 µL (0.44 mmol) of N,N-dicyclohexylamine and 95 mg (0.23 mmol) of the subtitled intermediate of Preparation 5. The resultant material was purified using column chromatography (eluent of ethyl acetate) to provide 125 mg of the desired titled product.

NMR (CD$_3$OD): δ8.2 (m, 2); 7.95 (m, 2); 7.83 (m, 2); 7.72 (t, 2); 7.55 (t, 2); 7.40 d, 2); 7.10 (m, 10); 4.70 (m, 4); 4.40 (t, 1); 4.15 (m, 2); 3.98 (m, 1); 3.85 m, 1); 3.38 (m, 1); 3.02 (s, 3); 2.97 s, 3); 2.55 (m, 4); 1.80 (m, 4); 1.58 m, 8); 0.97 (t, 6).

As noted above, the compounds of the present invention are useful for inhibiting HIV protease, which is an enzyme associated with vital component production and assembly. An embodiment of the present invention is a method of treating or preventing HIV infection comprising administering to a primate in need thereof an effective amount of a compound of formula I or a pharmaceutically acceptable salt thereof. Another embodiment of the present invention is a method of treating or preventing AIDS comprising administering to a primate in need thereof an effective amount of a compound of formula I or a pharmaceutically acceptable salt thereof. A further embodiment of the present invention is a method for inhibiting HIV replication comprising administering to an HIV infected cell or a cell susceptible to HIV infection a compound of formula I or a pharmaceutically acceptable salt thereof.

The term "effective amount" as used herein, means an amount of a compound of the present invention which is capable of inhibiting the HIV protease mediated vital component production and assembly. The HIV protease inhibition contemplated by the present method includes either therapeutic or prophylactic treatment, as appropriate. The specific dose of compound administered according to this invention to obtain therapeutic or prophylactic effects will, of course, be determined by the particular circumstances surrounding the case, including, for example, the compound administered, the route of administration, the condition being treated and the individual being treated. A typical daily dose will contain a dosage level of from about 0.01 mg/kg to about 50 mg/kg of body weight of an active compound of this invention. Preferred daily doses generally will be from about 0.05 mg/kg to about 20 mg/kg and ideally from about 0.1 mg/kg to about 10 mg/kg.

The compounds can be administered by a variety of routes including oral, rectal, transdermal, subcutaneous, intravenous, intramuscular and intranasal. The compounds of the present invention are preferably formulated prior to administration. Therefore, another embodiment of the present invention is a pharmaceutical formulation comprising an effective amount of a compound of Formula I or a pharmaceutically acceptable salt thereof and a pharmaceutically acceptable carrier, diluent or excipient therefor.

The active ingredient in such formulations comprises from 0.1% to 99.9% by weight of the formulation. By "pharmaceutically acceptable" it is meant that the carrier, diluent or excipient is compatible with the other ingredients of the formulation and not deleterious to the recipient thereof.

The present pharmaceutical formulations can be prepared by known procedures using well-known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders and the like.

The following formulation examples are illustrative only and are not intended to limit the scope of the invention in any way. The term "active ingredient" means a compound according to Formula I or a pharmaceutically acceptable salt thereof.

Formulation 1

Hard gelatin capsules are prepared using the following ingredients:

|  | Quantity (mg/capsule) |
| --- | --- |
| Active ingredient | 250 |
| Starch, dried | 200 |
| Magnesium stearate | 10 |
| Total | 460 mg |

Formulation 2

A tablet is prepared using the ingredients below:

|  | Quantity (mg/capsule) |
| --- | --- |
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
| --- | --- |
| Active ingredient | 0.25 |
| Methanol | 25.75 |
| Propellant 22 (Chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| Active ingredient | 60 mg |
|---|---|
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

| Active ingredient | 80 mg |
|---|---|
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
|---|---|
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| Active ingredient | 50 mg |
|---|---|
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

An intravenous formulation may be prepared as follows:

| Active ingredient | 100 mg |
|---|---|
| Isotonic saline | 1,000 mL |

The solution of the above ingredients generally is administered intravenously to a subject at a rate of 1 mL per minute.

The following experiment (Fluorescence HIV-1 Protease Inhibitor Assay) was carried out to demonstrate the ability of the compounds of the present invention to inhibit HIV protease.

As used herein, the abbreviations are defined as follows:

BSA—bovine serum albumin

BOC—t-butyloxycarbonyl

BrZ—2-bromobenzyloxycarbonyl

2-ClZ—2-chlorobenzyloxycarbonyl

DCC—dicyclohexylcarbodiimide

DIEA—diisopropylethylamine

DTT—dithiothreitol

EDTA—ethylenediaminetetraacetic acid

FITC—fluorescein isothiocarbamyl

HEPES—4-(2-hydroxyethyl)-1-piperazineethanesulfonic acid

MES—4 morpholineethanesulfonic acid

PAM—phenylacetimidomethyl

TAPS—3-[tris(hydroxymethyl)methyl]amino-1-sulfonic acid

TRIS—tris(hydroxymethyl)aminomethane

TOS—p-toluenesulfonyl (tosyl)

I. Preparation of Protease and Gag Fractions

A. Culture of *E. coli* K12 L507/pHP10D

Lyophils of *E. coli* K12 L507/pHP10D were obtained from the Northern Regional Research Laboratory, Peoria, Ill. 61604, under the accession number NRRL B-18560 (deposited Nov. 14, 1989). The lyophils were decanted into tubes containing 10 mL LB medium (10 g Bacto-tryptone, 5 g Bacto-yeast extract, and 10 g NaCl per liter; the pH was adjusted to 7.5 and incubated at 32° C., overnight).

A small portion of the overnight culture was placed on LB-agar (LB medium with 15 g/L Bacto-agar) plates containing 12.5 µg/mL tetracycline in a manner so as to obtain a single colony isolate of *E. coli* K12 L507/pHP10D. The single colony obtained was inoculated into 10 mL of LB medium containing 12.5 µg/mL tetracycline and incubated overnight at 32° C. with vigorous shaking. The 10 mL overnight culture was inoculated into LB medium containing 12.5 µg/mL tetracycline and incubated at 32° C. with vigorous shaking until the culture reached mid-log phase.

B. Culture of *E. coli* K12 L507/pHGAG

Lyophils of *E. coli* K12 L507/pHGAG were obtained from the NRRL under the accession number NRRL B-18561 (deposited Nov. 14, 1989). A purified colony of *E. coli* K 12 L507/pHGAG was isolated, and used as an inoculum for a culture which was grown to mid-log phase in substantial accordance with the teaching of Step A, above, for *E. coli* K12 L507/pHP10D.

C. Preparation of Protease Fraction

A culture of *E. coli* K12 L507/pHP10D was grown to mid-log phase at 32° C. in LB media containing 12.5 µg/ml tetracycline. The cultivation temperature was quickly elevated to 40° C. to induce gene expression, and the cells were allowed to grow for 2.5 hours at this temperature before the culture was quickly chilled on ice. The cells were centrifuged and the cell pellet was resuspended in 20 mL 50 mmol MES buffer (pH 6.0) containing 1 mmol EDTA, 1 mmol DTT, 1 mmol PMSF and 10% glycerol ("Buffer A"). Cells were lysed by sonication using a Fischer Model 300 Dismembrator and a microtip probe. Following centrifugation at 27,000 x g, the supernatant was diluted to a total volume of 60 mL with Buffer A and loaded onto a 2.0×19 cm QAE-Sepharose column (1 mL/min, 4° C.), that had been equilibrated in Buffer A. The column was washed isocratically for 180 min and then eluted with a gradient eluent of 0–1.0M NaCl in Buffer A over 120 min. Enzymatic activity was measured by HPLC using the synthetic peptide SQNYPIV as described in Margolin et al., *Biochem. Biophys. Res. Commun.*, 1.67, 554–560 (1990); the production of the p1 peptide (SQNY) was measured.

The active fractions were combined, made 1.2M in ammonium sulfate, and applied to a 2.0×18 cm hexyl agarose column that had been equilibrated in Buffer A containing 1.2M ammonium sulfate. The sample was loaded at a flow rate of 1 mL/min at 4° C., washed with the equilibration buffer for 240 min (1 mL/min) and then eluted using a reverse linear gradient of 1.2–0M ammonium sulfate in Buffer A for 120 min at the same flow rate. The column was then washed isocratically in Buffer A for 120 min.

The active fractions were combined, concentrated to 10 mL using an Amicon stirred cell with a YM-10 membrane and then applied to a MonoS cation exchange column (1.0×10 cm) that had been equilibrated in Buffer A. The sample was loaded at a flow rate of 1 mL/min at 25° C. After washing isocratically for 30 min, the protease was eluted using a linear gradient of 0–0.45M NaCl in Buffer A over 40 min. The column was washed isocratically in Buffer A containing 0.45M NaCl for 30 min.

The active fractions were combined and concentrated to 200 µL using an Amicon stirred cell and a YM-10 membrane and then the protease was applied to a Superose 6 size exclusion column equilibrated in Buffer A containing 0.1M NaCl. The column was washed isocratically in this buffer at a flow rate of 0.5 mL/min, following which the HIV protease was eluted as a single peak.

QAE-Sepharose, and hexyl agarose were purchased from Sigma Chemical Company. Superose 6 and MonoS were were purchased from Pharmacia. Buffers and reagents were obtained from Sigma.

D. Preparation of Gag Fraction

In an analogous manner, a culture of *E. coli* K12 507/pHGAG was grown to mid-log phase at 32° C. then shifted to 40° C. for about 4 to 5 hours. The culture was chilled on ice and centrifuged, then the pellet was resuspended in 8 mL lysis buffer containing 5 mg/mL lysozyme. Lysis buffer was comprised of 50 mM Tris-HCl (pH 7.8), 5 mM EDTA, 1 mM DTT, 100 mM NaCl, 1 µg/mL E64 and 2 µg/mL aprotinin. The culture was incubated about 30 to 60 minutes at 4° C., then briefly sonicated in a Branson® Cell Disrupter at 60% power, for three 20 second bursts with chilling between each burst. The culture was then centrifuged at 15,000 x g. The supernatant, which contains the unprocessed gag protein, was partially purified by size exclusion chromatography on a Sephadex G-50 column and stored at −20° C. in 50% glycerol and lysis buffer.

II. Preparation of Substrate $N^a$-Biotin-Gly-Ser-Gln-Asn-Tyr-Pro-Ile-Val-Gly-Lys($N^e$-FITC)-OH SEQ ID NO: 1.

A. Preparation of $N^a$-Biotin-Gly-Ser-Gln-Asn-Tyr-Pro-Ile-Val-Gly-Lys-OH SEQ ID NO: 3

The protected peptide-resin $N^a$-Boc-Gly-Ser-Gln-Asn-Tyr(BrZ)-Pro-Ile-Val-Gly-Lys(2-ClZ)-OCH$_2$-PAM-resin SEQ ID: 2 was synthesized on an Advanced Chemtech Model 200 peptide synthesizer at 1.5 mmol scale using the standard double-couple protocol. The amino terminal Boc group was removed with 50% trifluoroacetic acid in methylene chloride and the resulting resin neutralized with 5% di(isopropyl)ethylamine (DIEA) in methylene chloride. Then, 1.1 g (4.5 mmol) of biotin in 20 mL of dimethylsulfoxide was added to the peptide resin, followed by 4.5 mmol of dicyclohexylcarbodiimide (DCC) in 9 mL of methylene chloride. The resulting reaction mixture was diluted to 40 mL total volume using 11 mL methylene chloride, and then allowed to react for approximately 5 hours. The reaction solution was concentrated, the resin washed sequentially with dimethyl sulfoxide, dimethylformamide and methylene chloride and then neutralized with 5% DIEA in methylene chloride. This reaction was repeated twice, with the reaction time being extended to 12 hours per reaction. Ninhydrin analysis of the resin indicated complete reaction of the biotin with the glycine amine group. The final peptide resin was washed extensively with dimethylformamide and methylene chloride and dried to provide 4.3 g (98%).

B. Deprotection

The peptide was deprotected and cleaved from the resin using 50 mL of a hydrofluoric acid/m-cresol solution, 0° C., 1 hour. After removal of the hydrofluoric acid by vacuum distillation, the m-cresol was extracted from the reaction mixture using 100 mL diethyl ether. The peptide was then solubilized in 50% aqueous acetic acid, frozen and lyophilized to provide 2.14 g.

C. Purification

The crude $N^\alpha$-Biotin-Gly-Ser-Gln-Asn-Tyr-Pro-Ile-Val-Gly-Lys-OH SEQ ID: 3 was dissolved in 200 mL of a 5% acetonitrile (aqueous) solution containing 0.1% trifluoroacetic acid and then filtered through a 0.22 micron filter. The resulting solution was applied to a 2.2×25 cm. reverse phase column of octadecyl-silica (Vydac C-18) which had been equilibrated with the same buffer. The peptide was eluted using an 855 minute linear gradient of 7.5–25% acetonitrile, at 2 mL/minute, with collection of fractions. These fractions were analyzed using Analytical HPLC was performed on a 4.6×250 mm Vydac C-18 column using similar buffer conditions. The fractions containing the desired material were combined, frozen and lyophilized to provide 1.206 g (62%).

Amino acid analysis of the isolated $N^\alpha$-Biotin-Gly-Ser-Gln-Asn-Tyr-Pro-Ile-Val-Gly-Lys-OH SEQ ID NO: 3 gave the following ratios: Asn 1.1; Ser 0.96; Gln 1.1; Pro 1.1; Gly 2.1; Val 0.80; Ile 0.78; Tyr 1.1; Lys 1.1; in agreement with theory. Fast-atom bombardment mass spectrometry gave a molecular ion mass peak of 1288, in agreement with theory.

D. Labeling

The purified peptide was labeled with a fluorescent marker at the C-terminal end for use in the Pandex assay. $N^\alpha$-Biotin-Gly-Ser-Gln-Asn-Tyr-Pro-Ile-Val-Gly-Lys-OH SEQ ID NO: 3 (1.206 g, 0.936 mmol) was dissolved in 100 mL of 0.1M sodium borate, pH 9.5. Then, a solution of 3 g (7.7 mmol) of fluorescein isothiocyanate in 15 mL dimethyl sulfoxide was added to the reaction mixture in 10 equal portions over two hours. The resulting mixture was allowed to react for one hour after the final addition. The solution was adjusted to pH 3 using 5N HCl, resulting in the formation of a precipitate which was removed by centrifugation.

The peptide solution was then adjusted to pH 7.8 using 5N sodium hydroxide and then diluted to 200 mL total volume by the addition of 0.1M ammonium acetate, pH 7.5. The resulting solution was then filtered through a 0.22 micron filter and loaded onto a 2.2×25 cm column of Vydac C-18 which had been equilibrated with of 5% acetonitrile in 0.1M ammonium acetate (pH 7.5). The peptide was eluted from the column using an 855 minute linear gradient of 5–25% acetonitrile, at 2 mL/minute, with collection of fractions. Analytical HPLC was used to analyze the fractions. The fractions containing the desired product were then combined, frozen and lyophilized to provide 190.2 mg (12%).

Amino acid analysis of the purified peptide gave the following: Asn 1.1; Set 1.0; Gln 1.1: Pro 1.1; Gly 2.1; Val 0.8; Ile 0.8; Tyr 1.1; Lys 1.0; in agreement with theory. Fast-atom bombardment mass spectrometry gave a molecular ion mass peak of 1678, in agreement with theory.

E. Fluorescence HIV-1 Protease Inhibitor Assay

The following buffers and solutions are used in the Fluorescence HIV-1 Protease Inhibitor Assay:

| MES-ALB Buffer: | 0.05 M 4-morpholineethane sulfonic acid, pH 5.5 |
| | 0.02 M NaCl |
| | 0.002 M EDTA |
| | 0.001 M DTT |
| | 1.0 mg/mL BSA |
| TBSA Buffer: | 0.02 M TRIS |
| | 0.15 M NaCl |
| | 1.0 mg/mL BSA |
| Avidin Coated Beads Solution: | 0.1% solution of Fluoricon Avidin Assay Particles (Avidin conjugated to solid polystyrene beads, 0.6–0.8 microns in diameter in TBSA Buffer |
| Enzyme Solution: | 27 IU/mL of purified HIV-1 protease in MES-ALB buffer (1 IU equals the amount of enzyme required to hydrolyze 1 μmole of substrate per minute at 37° C. |

To each well of a round bottom, 96-well plate is added 20 μL of the Enzyme Solution followed by 10 μL of the compound to be evaluated in a 20% aqueous dimethylsulfoxide solution. Purified HIV-1 protease was obtained as described above. The resulting solution is incubated for one hour at room temperature and then 20 μL of a solution containing the substrate, $N^\alpha$-Biotin-Gly-Ser-Gln-Asn-Tyr-Pro-Ile-Val-Gly-Lys($N^\epsilon$ -FITC)-OH, in MES-ALB buffer (1.5 μL/mL) is added to each well. The solutions are then incubated for 16 hours at room temperature and then each well is diluted with 150 μL of MES-ALB buffer.

To each well of a second round bottom, 96-well Pandex plate is added 25 uL of the Avidin Coated Beads Solution. Then, to each well is added 25 μL of the diluted incubation solutions, prepared above. The solutions are mixed thoroughly and the plates are loaded into a Pandex® machine, washed, evacuated and read. Sample detection was performed by excitation at 485 nm, reading the resulting epifluorescence at 535 nm.

The $IC_{50}$ results obtained in the Fluorescence Assay for the compounds of the present invention are set forth below in Table 1. All values have been normalized to a positive control which is [1S-(1R*,4R*,5S*)]-N-(1-(2-amino-2-oxoethyl)-2-oxo-3-aza-4-phenylmethyl-5-hydroxy-6-(2-(1-t-butylamino-1-oxomethyl)phenyl)hexyl)-2-quinolinyl carboxamide.

TABLE 1

| Inhibitory Activity of Formula I Compounds | |
|---|---|
| Example No. | Fluorescence Assay $IC_{50}$ in ng/ml |
| Control | 1.0 |
| 1 | 159* |
| 2 | 10.4 |
| 3 | 4200 |
| 4 | 51* |
| 5 | n.t. |
| 6 | 654 |
| 7 | 6810 |
| 8 | 262* |
| 9 | 69.5 |
| 10 | 1.8 |
| 11 | 195* |
| 12 | 1393 |
| 13 | 2245 |
| 14 | 183 |
| 15 | 24 |
| 16 | $IC_{32}$(1000) |
| 17 | 20.5* |
| 18 | 7.1* |
| 19 | 150* |
| 20 | 556 |
| 21 | 58 |
| 22 | 396 |
| 23 | 497 |

TABLE 1-continued

Inhibitory Activity of Formula I Compounds

| Example No. | Fluorescence Assay $IC_{50}$ in ng/ml |
|---|---|
| 24 | 131 |
| 25 | $IC_{40}(1000)$ |
| 26 | $IC_{23}(1000)$ |
| 27 | 26.7 |
| 28 | 817 |
| 29 | 30.5 |
| 30 | 336 |
| 31 | 25.2 |
| 32 | 172* |
| 33 | $IC_{25}(1000)$ |
| 34 | $IC_{34}(1000)$ |
| 35 | $IC_{23}(1000)$ |
| 36 | $IC_{26}(1000)$ |
| 37 | 166 |
| 38 | 21.5 |

*average $IC_{50}$
n.t. not tested

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1..2
        ( D ) OTHER INFORMATION: /label= Modified-site
            / note="The alpha amino group of glycine at position one is biotinylated."

( i x ) FEATURE:
        ( A ) NAME/KEY: Modified-site
        ( B ) LOCATION: 9..10
        ( D ) OTHER INFORMATION: /label= Modified-site
            / note="The epsilon amino group of lysine at position 10 of the peptide has been derivatized with FITC."

( x i ) SEQUENCE DESCRIPTION: SEQ ID NO:1:

Gly Ser Gln Asn Tyr Pro Ile Val Gly Lys
1                 5                           10

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1..2
        ( D ) OTHER INFORMATION: /label= Modified-site
            / note="The alpha amino of glycine at position one with t-butoxycarbonyl."

( i x ) FEATURE:
        ( A ) NAME/KEY: Active-site
        ( B ) LOCATION: 5..6
        ( D ) OTHER INFORMATION: /label= modified-site -continued / note="2-bromobenzyloxycarbonyl is used as a side chain protecting group in the solid phase preparation of the peptide."

( i x ) FEATURE:
  ( A ) NAME/KEY: Modified-site
  ( B ) LOCATION: 9..10
  ( D ) OTHER INFORMATION: /label= modified-site
    / note="The epsilon amino group of the lysine is derivatized with 2-chlorobenzyloxycarbonyl. The carboxy terminus is linked to a PAM resin.

( x i ) SEQUENCE DESCRIPTION: SEQ ID NO:2:

Gly Ser Gln Asn Tyr Pro Ile Val Gly Lys
1               5                   10

( 2 ) INFORMATION FOR SEQ ID NO:3:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1..2
    ( D ) OTHER INFORMATION: /label= modified-site
      / note="The alpha amino group of glycine at position one is biotinylated."

( x i ) SEQUENCE DESCRIPTION: SEQ ID NO:3:

Gly Ser Gln Asn Tyr Pro Ile Val Gly Lys
1               5                   10

We claim:

1. A compound of formula I wherein:

R is $C_1-C_6$ alkyl, cycloalkyl, a 5- to 7- member monocyclic or 7- to 10- member bicyclic heterocycle, which has 0–5 double bonds, and consists of carbon atoms and from one to three heteroatoms selected from nitrogen, oxygen and sulfur and, wherein, any nitrogen and sulfur heteroatoms are oxidized or unoxidized and, any nitrogen heteroatom is quaternized or unquaternized, aryl, cycloalkyl($C_1-C_4$)alkyl, heterocycle($C_1-C_4$)alkyl, wherein said heterocycle has the same meanings as defined above, aryl($C_1-C_4$)alkyl, or —A—$(CH_2)_q$—$R^0$, where A is —O—, —NH— or —S—;

q is 0, 1, 2, or 3;

$R^0$ is cycloalkyl, aryl, heterocycle, as defined above;

X is where:

$R^1$ is aryl, cycloalkyl, heterocycle as defined above;

$R^2$ is hydrogen or $C_1-C_4$ alkyl;

$R^3$ is an amino acid side chain, —$CH_2CH_3$, —$CH_2CH_2CH_3$, —$CH_2(CH_2)_2CH_3$, —$C(CH_3)_3$, cyano($C_1-C_4$)alkyl, heterocycle($C_1-C_4$)alkyl as defined above, aryl($C_1-C_4$)alkyl or —$(CH_2)_s$—$A^0$—$(CH_2)_r$—$R^4$ or —$CH_2$—$C(O)$—$NR^2$—$(CH_2)_r$—$R^5$, where s is 1, 2, 3, or 4;

r is 0, 1, 2, or 3;

$A^0$ is —O—, —NH— or —S—;

$R^4$ is $C_1-C_6$ alkyl, cycloalkyl, aryl, or heterocycle as defined above;

$R^5$ is cycloalkyl, aryl, or heterocycle as defined above;

j is 0, 1, 2, 3, or 4;

k is 0 or 1; and

Y is —O—, —N($R^2$)— or —S—;

or a pharmaceutically acceptable salt thereof.

2. A compound according to claim 1 wherein:
X is

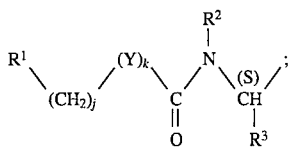

R is aryl, aryl($C_1$-$C_4$)alkyl or —A—$(CH_2)_q$—$R^0$, where
  A is —S—;
  q is 0;
  $R^0$ is aryl;
$R^1$ is aryl or heterocycle;
j is 0, 1 or 2;
Y is —O— or —N($R^2$)—;
k is 1;
$R^2$ is hydrogen or methyl;
$R^3$ is an amino acid side chain, —$CH_2CH_3$, —$CH_2CH_2CH_3$, —$CH_2(CH_2)_2CH_3$, —$C(CH_3)_3$ or —$CH_2$—C(O)—$NR^2$—$(CH_2)_r$—$R^5$, where
  r is 0, 1, 2 or 3; and
  $R^5$ is cycloalkyl, aryl, or a heterocycle;
or a pharmaceutically acceptable salt thereof.

3. A compound according to claim 2 wherein:
R is phenyl, phenylthio, naphthyl, naphthylthio, phenylethyl or naphthylethyl;
$R^1$ is phenyl, naphthyl or quinolinyl;
j is 1;
$R^2$ is hydrogen;
$R^3$ is an amino acid side chain, —$CH_2CH_3$ or —$CH_2$—C(O)—$NR^2$—$(CH_2)_r$—$R^5$, where
  r is 0, 1, 2 or 3;
  $R^5$ is aryl or a heterocycle;
or a pharmaceutically acceptable salt thereof.

4. A compound according to claim 3 wherein:
R is phenyl or phenylethyl;
$R^1$ is phenyl or quinolinyl; and
$R^3$ is —$CH_2CH_3$ or —CH($CH_3$)$_2$;
or a pharmaceutically acceptable salt thereof.

5. The compound according to claim 4 which is 1,6-diphenyl-2(S),5(S)-di[N-[2(S)-N[(quinolin-2-ylmethoxy)carbonyl]aminobutanoyl]amino]-3,4-cis-epoxyhexane or a pharmaceutically acceptable salt thereof.

6. The compound according to claim 4 which is 1,6-diphenyl-2(S),5(S)-di[N-[2(S)-N-[[N(methyl)-N(quinolin-2-ylmethyl)amino]carbonyl]aminobutanoyl]amino]-3,4-cis-epoxyhexane or a pharmaceutically acceptable salt thereof.

7. The compound according to claim 4 which is 1,6-diphenyl-2(S),5(S)-di[N-[2(S)-N[(8-fluoroquinolin-2-ylmethoxy)carbonyl]amino-3-methylbutanoyl]amino]-3,4-cis-epoxyhexane or a pharmaceutically acceptable salt thereof.

8. The compound according to claim 4 which is 1,10-diphenyl-4(S),7(S)-di[N-[2(S)-N-[[N(methyl)-N(quinolin-2-ylmethyl)amino]carbonyl]aminobutanoyl]amino]-5,6-cis-epoxydecane or a pharmaceutically acceptable salt thereof.

9. A pharmaceutical formulation comprising one or more pharmaceutically acceptable carriers and a compound of claim 1.

10. A pharmaceutical formulation according to claim 9 where the compound is one wherein:

X is

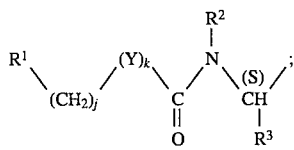

R is aryl, aryl($C_1$-$C_4$)alkyl or —A—$(CH_2)_q$—$R^0$, where
  A is —S—;
  q is 0;
  $R^0$ is aryl;
$R^1$ is aryl or a heterocycle;
j is 0, 1 or 2;
Y is —O— or —N($R^2$)—;
k is 1;
$R^2$ is hydrogen or methyl;
$R^3$ is an amino acid side chain, —$CH_2CH_3$, —$CH_2CH_2CH_3$, —$CH_2(CH_2)_2CH_3$, —$C(CH_3)_3$ or —$CH_2$—C(O)—$NR^2$—$(CH_2)_r$—$R^5$, where
  r is 0, 1, 2 or 3; and
  $R^5$ is cycloalkyl, aryl, or a heterocycle;
or a pharmaceutically acceptable salt thereof.

11. A pharmaceutical formulation according to claim 10 where the compound is one wherein:
R is phenyl, phenylthio, naphthyl, naphthylthio, phenylethyl or naphthylethyl;
$R^1$ is phenyl, naphthyl or quinolinyl;
j is 1;
$R^2$ is hydrogen;
$R^3$ is an amino acid side chain, —$CH_2CH_3$ or —$CH_2$—C(O)—$NR^2$—$(CH_2)_r$—$R^5$, where
  r is 0, 1, 2 or 3; and
  $R^5$ is aryl or a heterocycle;
or a pharmaceutically acceptable salt thereof.

12. A pharmaceutical formulation according to claim 11 where the compound is one wherein:
R is phenyl or phenylethyl;
$R^1$ is phenyl or quinolinyl; and
$R^3$ is —$CH_2CH_3$ or —CH($CH_3$)$_2$;
or a pharmaceutically acceptable salt thereof.

13. A pharmaceutical formulation according to claim 12 where the compound is 1,6-diphenyl-2(S),5(S)-di[N-[2(S)-N[(quinolin-2-ylmethoxy)carbonyl]aminobutanoyl]amino]-3,4-cis-epoxyhexane or a pharmaceutically acceptable salt thereof.

14. A pharmaceutical formulation according to claim 12 where the compound is 1,6-diphenyl-2(S),5(S)-di[N-[2(S)-N-[[N(methyl)-N(quinolin-2-ylmethyl)amino]carbonyl]aminobutanoyl]amino]-3,4-cis-epoxyhexane or a pharmaceutically acceptable salt thereof.

15. A pharmaceutical formulation according to claim 12 where the compound is 1,6-diphenyl-2(S),5(S)di[N-[2(S)-N[(8-fluoroquinolin-2-ylmethoxy)carbonyl]amino-3-methylbutanoyl]amino]-3,4-cis-epoxyhexane or a pharmaceutically acceptable salt thereof.

16. A pharmaceutical formulation according to claim 12 where the compound is 1,10-diphenyl-4(S),7(S)-di[N-[2(S)-N-[[N(methyl)-N(quinolin-2-ylmethyl)amino]carbonyl]aminobutanoyl]amino]-5,6-cis-epoxydecane or a pharmaceutically acceptable salt thereof.

17. A method of treating HIV infection comprising administering to a primate in need of thereof, an effective amount of a compound of the claim 1.

18. The method according to claim 17 where the compound is one wherein:

X is

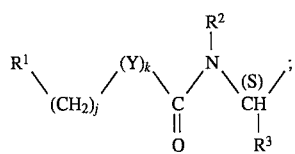

R is aryl, aryl($C_1$-$C_4$)alkyl or —A—$(CH_2)_q$—$R^0$, where
A is —S—;
q is 0;
$R^0$ is aryl;
$R^1$ is aryl or a heterocycle;
j is 0, 1 or 2;
Y is —O— or —N($R^2$)—;
k is 1;
$R^2$ is hydrogen or methyl;
$R^3$ is an amino acid side chain, —$CH_2CH_3$, —$CH_2CH_2CH_3$, —$CH_2(CH_2)_2CH_3$, —$C(CH_3)_3$ or —$CH_2$—C(O)—$NR^2$—$(CH_2)_r$—$R^5$, where
r is 0, 1, 2 or 3; and
$R^5$ is cycloalkyl, aryl, or a heterocycle;
or a pharmaceutically acceptable salt thereof.

19. The method according to claim 18 where the compound is one wherein:

R is phenyl, phenylthio, naphthyl, naphthylthio, phenylethyl or naphthylethyl;
$R^1$ is phenyl, naphthyl or quinolinyl;
j is 1;
$R^2$ is hydrogen;
$R^3$ is an amino acid side chain, —$CH_2CH_3$ or —$CH_2$—C(O)—$NR^2$—$(CH_2)_r$—$R^5$, where
r is 0, 1, 2 or 3; and
$R^5$ is aryl or a heterocycle;
or a pharmaceutically acceptable salt thereof.

20. The method according to claim 19 where the compound is one wherein:

R is phenyl or phenylethyl;
$R^1$ is phenyl or quinolinyl; and
$R^3$ is —$CH_2CH_3$ or —$CH(CH_3)_2$;
or a pharmaceutically acceptable salt thereof.

21. The method according to claim 20 where the compound is 1,6-diphenyl-2(S),5(S)-di[N-[2(S)-N[(quinolin-2-ylmethoxy)carbonyl]aminobutanoyl]amino]-3,4-cis-epoxyhexane or a pharmaceutically acceptable salt thereof.

22. The method according to claim 20 where the compound is 1,6-diphenyl-2(S),5(S)-di[N-[2(S)-N[[N(methyl)-N(quinolin-2-ylmethyl)amino]carbonyl]aminobutanoyl]amino]-3,4-cis-epoxyhexane or a pharmaceutically acceptable salt thereof.

23. The method according to claim 20 where the compound is 1,6-diphenyl-2(S),5(S)-di[N-[2(S)-N[(8-fluoroquinolin-2-ylmethoxy)carbonyl]-amino-3-methylbutanoyl]amino]-3,4-cis-epoxyhexane or a pharmaceutically acceptable salt thereof.

24. The method according to claim 20 where the compound is 1,10-diphenyl-4(S),7(S)-di[N-[2(S)-N[[N(methyl)-N(quinolin-2-ylmethyl)amino]carbonyl]aminobutanoyl]amino]-5,6-cis-epoxydecane or a pharmaceutically acceptable salt thereof.

* * * * *